United States Patent
Marquardt et al.

(10) Patent No.: US 11,166,932 B2
(45) Date of Patent: Nov. 9, 2021

(54) STIMULATORS AND/OR ACTIVATORS OF SOLUBLE GUANYLATE CYCLASE (SGC) IN COMBINATION WITH AN INHIBITOR OF NEUTRAL ENDOPEPTIDASE (NEP INHIBITOR) AND/OR AN ANGIOTENSIN AII ANTAGONIST AND THE USE THEREOF

(71) Applicant: BAYER PHARMA AKTIENGESELLSCHAFT, Berlin (DE)

(72) Inventors: Tobias Marquardt, Wuppertal (DE); Markus Follmann, Cologne (DE); Johannes-Peter Stasch, Grottaferrata (IT)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/746,624

(22) PCT Filed: Jul. 15, 2016

(86) PCT No.: PCT/EP2016/066891
§ 371 (c)(1),
(2) Date: Jan. 11, 2019

(87) PCT Pub. No.: WO2017/013010
PCT Pub. Date: Jan. 26, 2017

(65) Prior Publication Data
US 2019/0125709 A1    May 2, 2019

(30) Foreign Application Priority Data
Jul. 23, 2015 (EP) .................................. 15178141

(51) Int. Cl.
| | | |
|---|---|---|
| A61K 31/216 | (2006.01) | |
| A61K 31/41 | (2006.01) | |
| A61K 45/06 | (2006.01) | |
| A61K 31/506 | (2006.01) | |
| A61K 31/519 | (2006.01) | |

(52) U.S. Cl.
CPC ........... *A61K 31/216* (2013.01); *A61K 31/41* (2013.01); *A61K 31/506* (2013.01); *A61K 31/519* (2013.01); *A61K 45/06* (2013.01)

(58) Field of Classification Search
CPC .. A61K 2300/00; A61K 31/216; A61K 31/41; A61K 31/506; A61K 31/519; A61K 45/06; A61P 11/00; A61P 13/12; A61P 3/06; A61P 3/14; A61P 43/00; A61P 7/02; A61P 7/10; A61P 9/00; A61P 9/04
USPC ....................................................... 514/381
See application file for complete search history.

(56) References Cited

U.S. PATENT DOCUMENTS

| | | | |
|---|---|---|---|
| 5,217,996 A * | 6/1993 | Ksander | ................ C07C 233/47 514/533 |
| 5,399,578 A * | 3/1995 | Buhlmayer | ........... C07C 229/38 514/381 |
| 6,166,027 A | 12/2000 | Straub et al. | |
| 6,180,656 B1 | 1/2001 | Fürstner et al. | |
| 6,451,805 B1 | 9/2002 | Straub et al. | |
| 6,693,102 B2 | 2/2004 | Stasch et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 6,903,089 B1 | 6/2005 | Stasch et al. | |
| 6,919,345 B2 | 7/2005 | Stasch et al. | |
| 6,939,989 B2 | 9/2005 | Härter et al. | |
| 7,067,694 B2 | 6/2006 | Härter et al. | |
| 7,087,644 B1 | 8/2006 | Alonso-Alija et al. | |
| 7,091,198 B1 | 8/2006 | Feurer et al. | |
| 7,105,523 B2 | 9/2006 | Stasch et al. | |
| 7,115,599 B2 | 10/2006 | Stasch et al. | |
| 7,135,474 B2 | 11/2006 | Weigand et al. | |
| 7,173,037 B2 | 2/2007 | Alonso-Alija et al. | |
| 7,329,777 B2 | 2/2008 | Harter et al. | |

(Continued)

FOREIGN PATENT DOCUMENTS

| | | |
|---|---|---|
| EP | 0 443 983 A1 | 8/1991 |
| EP | 0 555 175 A1 | 8/1993 |

(Continued)

OTHER PUBLICATIONS

Goldblatt et al., "The Effect of Main Artery Occlusion of one Kidney on Blood Pressure of Dog," Proceedings of the National Academy of Sciences of the United States of America, (May 1976), vol. 73, No. 5, pp. 1722-1724.
Gu et al., "Pharmacokinetics and Pharmacodynamics of LCZ696, a Novel Dual-Acting Angiotensin Receptor-Neprilysin Inhibitor (ARNi)," Journal of clinical pharmacology, (Apr. 2010), vol. 50, No. 4, pp. 401-414.
Komajda et al., "Heart Failure with Preserved Ejection Fraction: a Clinical Dilemma," European Heart Journal, (Apr. 2014), vol. 34, No. 16, pp. 1022-1032.

(Continued)

*Primary Examiner* — Tracy Vivlemore
*Assistant Examiner* — Ebenezer O Sackey
(74) *Attorney, Agent, or Firm* — Quarles & Brady LLP

(57) ABSTRACT

The present invention relates to stimulators and activators of soluble guanylate cyclase in combination with an inhibitor of neutral endopeptidase and/or angiotensin AII antagonists and the use thereof for the treatment and/or prophylaxis of cardiovascular disorders, for example heart failure with preserved ejection fraction or heart failure with reduced ejection fraction, renal disorders, for example chronic kidney failure, urological disorders, lung disorders, disorders of the central nervous system, for regulation of cerebral perfusion, for example in the event of vascular cerebral states of dementia, for the treatment and/or prophylaxis of fibrotic disorders and other disease symptoms (e.g. end organ damage affecting the brain, kidney or heart).

16 Claims, 5 Drawing Sheets

(56) References Cited

U.S. PATENT DOCUMENTS

| | | | |
|---|---|---|---|
| 7,371,777 B2* | 5/2008 | Clark | C07C 233/87 514/365 |
| 7,468,390 B2* | 12/2008 | Ksander | A61K 31/192 514/381 |
| 7,468,590 B1* | 12/2008 | Krishnamoorthy | G11B 19/2054 318/268 |
| 7,674,825 B2 | 3/2010 | Alonso-Alija et al. | |
| 7,985,876 B2 | 7/2011 | Hahn et al. | |
| 7,998,988 B2 | 8/2011 | Bartel et al. | |
| 8,101,659 B2* | 1/2012 | Ksander | A61K 31/192 514/381 |
| 8,114,400 B2 | 2/2012 | Schirok et al. | |
| 8,168,821 B2 | 5/2012 | Becker et al. | |
| 8,173,704 B2 | 5/2012 | Bartel et al. | |
| 8,183,271 B2 | 5/2012 | Bartel et al. | |
| 8,217,063 B2 | 7/2012 | Hahn et al. | |
| 8,309,551 B2 | 11/2012 | Schirok et al. | |
| 8,420,656 B2 | 4/2013 | Follmann et al. | |
| 8,461,348 B2 | 6/2013 | Matsunaga et al. | |
| 8,609,727 B2 | 12/2013 | Bartel et al. | |
| 8,642,592 B2 | 2/2014 | Lampe et al. | |
| 8,673,903 B2 | 3/2014 | Hübsch et al. | |
| 8,765,769 B2 | 7/2014 | Follmann et al. | |
| 8,778,964 B2 | 7/2014 | Vakalopoulos et al. | |
| 8,796,305 B2 | 8/2014 | Vakalopoulos et al. | |
| 8,796,331 B2* | 8/2014 | Ksander | A61K 31/192 514/381 |
| 8,796,335 B2* | 8/2014 | Hahn | A61K 45/06 514/563 |
| 8,859,569 B2 | 10/2014 | Follmann et al. | |
| 8,981,104 B2 | 3/2015 | Hahn et al. | |
| 8,987,256 B2 | 3/2015 | Hahn et al. | |
| 9,018,258 B2 | 4/2015 | Lampe et al. | |
| 9,023,849 B2 | 5/2015 | Follmann et al. | |
| 9,090,609 B2 | 7/2015 | Follmann et al. | |
| 9,090,610 B2 | 7/2015 | Follmann et al. | |
| 9,096,592 B2 | 8/2015 | Follmann et al. | |
| 9,126,998 B2 | 9/2015 | Vakalopoulos et al. | |
| 9,133,191 B2 | 9/2015 | Follmann et al. | |
| 9,150,580 B2 | 10/2015 | Follmann et al. | |
| 9,216,978 B2 | 12/2015 | Follmann et al. | |
| 9,266,871 B2 | 2/2016 | Follmann et al. | |
| 9,278,968 B2 | 3/2016 | Kurosaki et al. | |
| 9,309,198 B2 | 4/2016 | Lampe et al. | |
| 9,309,239 B2 | 4/2016 | Follmann et al. | |
| 9,387,203 B2 | 7/2016 | Hübsch et al. | |
| 9,422,285 B2 | 8/2016 | Vakalopoulos et al. | |
| 9,447,090 B2 | 9/2016 | Koga et al. | |
| 9,498,480 B2 | 11/2016 | Follmann et al. | |
| 9,605,008 B2 | 3/2017 | Vakalopoulos et al. | |
| 9,776,997 B2 | 10/2017 | Vakalopoulos et al. | |
| 9,951,450 B2 | 4/2018 | Joung et al. | |
| 10,150,773 B2* | 12/2018 | Vakalopoulos | C07D 487/04 |
| 2004/0053915 A1 | 3/2004 | Geiss et al. | |
| 2004/0082798 A1 | 4/2004 | Alonso-Alija et al. | |
| 2004/0176446 A1 | 9/2004 | Alonso-Alija et al. | |
| 2004/0235863 A1 | 11/2004 | Feurer et al. | |
| 2008/0262059 A1* | 10/2008 | Ksander | A61K 31/192 514/381 |
| 2010/0004235 A1 | 1/2010 | Schirok et al. | |
| 2010/0113507 A1 | 5/2010 | Fürstner et al. | |
| 2011/0130445 A1 | 6/2011 | Lampe et al. | |
| 2012/0028971 A1* | 2/2012 | Lampe | A61K 31/4035 514/229.2 |
| 2012/0029002 A1 | 2/2012 | Straub et al. | |
| 2013/0079412 A1* | 3/2013 | Hahn | A61K 45/06 514/563 |
| 2014/0171434 A1 | 6/2014 | Follmann et al. | |
| 2014/0228366 A1 | 8/2014 | Follmann et al. | |
| 2014/0309307 A1* | 10/2014 | Hahn | A61K 45/06 514/563 |
| 2014/0357637 A1 | 12/2014 | Follmann et al. | |
| 2016/0002267 A1 | 1/2016 | Follmann et al. | |
| 2016/0122341 A1* | 5/2016 | Vakalopoulos | C07D 471/04 514/210.21 |
| 2016/0176880 A1 | 6/2016 | Vakalopoulos et al. | |
| 2016/0264515 A1* | 9/2016 | Hahn | A61K 45/06 |
| 2017/0313700 A1 | 11/2017 | Vakalopoulos et al. | |

FOREIGN PATENT DOCUMENTS

| | | |
|---|---|---|
| EP | 1 948 158 A1 | 7/2008 |
| WO | 98/16223 A1 | 4/1998 |
| WO | 98/16507 A2 | 4/1998 |
| WO | 98/23619 A1 | 6/1998 |
| WO | 00/02851 A1 | 1/2000 |
| WO | 00/06568 A1 | 2/2000 |
| WO | 00/06569 A1 | 2/2000 |
| WO | 01/19776 A2 | 3/2001 |
| WO | 01/19778 A1 | 3/2001 |
| WO | 01/19780 A2 | 3/2001 |
| WO | 2011/056511 A2 | 5/2001 |
| WO | 02/36120 A1 | 5/2002 |
| WO | 02/42299 A1 | 5/2002 |
| WO | 02/42300 A1 | 5/2002 |
| WO | 02/42301 A1 | 5/2002 |
| WO | 02/42302 A1 | 5/2002 |
| WO | 02/070459 A1 | 9/2002 |
| WO | 02/070460 A1 | 9/2002 |
| WO | 02/070461 A1 | 9/2002 |
| WO | 02/070462 A1 | 9/2002 |
| WO | 02/070510 A2 | 9/2002 |
| WO | 02/092596 A1 | 11/2002 |
| WO | 03/004503 A1 | 1/2003 |
| WO | 03/009545 A2 | 1/2003 |
| WO | 03/095451 A1 | 11/2003 |
| WO | 03/097063 A1 | 11/2003 |
| WO | 2004/009589 A1 | 1/2004 |
| WO | 2007/045366 A1 | 4/2007 |
| WO | 2007/045367 A1 | 4/2007 |
| WO | 2007/045369 A1 | 4/2007 |
| WO | 2007/045370 A1 | 4/2007 |
| WO | 2007/045433 A1 | 4/2007 |
| WO | 2007/056546 A1 | 5/2007 |
| WO | 2007/124854 A1 | 11/2007 |
| WO | 2007/128454 A1 | 11/2007 |
| WO | 2008/031513 A1 | 3/2008 |
| WO | 2008/061657 A1 | 5/2008 |
| WO | 2008/119457 A2 | 10/2008 |
| WO | 2008/119458 A1 | 10/2008 |
| WO | 2009/032249 A1 | 3/2009 |
| WO | 2009/068652 A1 | 6/2009 |
| WO | 2009/071504 A1 | 6/2009 |
| WO | 2009/123316 A1 | 10/2009 |
| WO | 2009/127338 A1 | 10/2009 |
| WO | 2010/065275 A1 | 6/2010 |
| WO | 2010/079120 A1 | 7/2010 |
| WO | 2010/102717 A1 | 9/2010 |
| WO | 2011/051165 A1 | 5/2011 |
| WO | 2011/115804 A1 | 9/2011 |
| WO | 2011/119518 A1 | 9/2011 |
| WO | 2011/141409 A1 | 11/2011 |
| WO | 2011/147809 A1 | 12/2011 |
| WO | 2011/149921 A1 | 12/2011 |
| WO | 2012/003405 A1 | 1/2012 |
| WO | 2012/004258 A1 | 1/2012 |
| WO | 2012/004259 A1 | 1/2012 |
| WO | 2012/028647 A1 | 3/2012 |
| WO | 2012/059548 A1 | 5/2012 |
| WO | 2012/059549 A1 | 5/2012 |
| WO | 2012/064559 A1 | 5/2012 |
| WO | 2012/076466 A2 | 6/2012 |
| WO | 2012/139888 A1 | 10/2012 |
| WO | 2012/143510 A1 | 10/2012 |
| WO | 2012/152629 A1 | 11/2012 |
| WO | 2012/152630 A1 | 11/2012 |
| WO | 2012/165399 A1 | 12/2012 |
| WO | 2013/004785 A1 | 1/2013 |
| WO | 2013/030288 A1 | 3/2013 |
| WO | 2013/104597 A1 | 7/2013 |
| WO | 2013/104598 A2 | 7/2013 |
| WO | 2013/104703 A1 | 7/2013 |

(56) References Cited

FOREIGN PATENT DOCUMENTS

| WO | 2013/131923 A1 | 9/2013 |
|---|---|---|
| WO | 2013/174736 A1 | 11/2013 |
| WO | 2014/012934 A1 | 1/2014 |
| WO | 2014/012935 A1 | 1/2014 |
| WO | 2014/047111 A1 | 3/2014 |
| WO | 2014/047325 A1 | 3/2014 |
| WO | 2014/068095 A1 | 5/2014 |
| WO | 2014/068099 A1 | 5/2014 |
| WO | 2014/068104 A1 | 5/2014 |
| WO | 2014/084312 A1 | 6/2014 |
| WO | 2014/128109 A1 | 8/2014 |
| WO | 2014/131741 A1 | 9/2014 |
| WO | 2014/131760 A1 | 9/2014 |
| WO | 2014/144100 A2 | 9/2014 |
| WO | 2014/195333 A1 | 12/2014 |
| WO | 2015/004105 A1 | 1/2015 |
| WO | 2015/008885 A1 | 1/2015 |
| WO | 2015/008886 A1 | 1/2015 |
| WO | 2015/018808 A1 | 2/2015 |
| WO | 2015/018814 A1 | 2/2015 |
| WO | 2016/087342 A1 | 6/2016 |

OTHER PUBLICATIONS

McMurray et al., "Angiotensin-Neprilysin Inhibition versus Enalapril in Heart Failure," The New England Journal of Medicine, (Sep. 11, 2014), vol. 371, No. 11, pp. 993-1004.

Page et al., "A Method for Producing Persistent Hypertension by Cellophane," Science, (Mar. 24, 1939), vol. 89, No. 2308, pp. 273-274.

Redfield et al., "Cardiorenal and Neurohumoral Function in a Canine Model of Early Left Ventricular Dysfunction," Circulation, (Jun. 1993), vol. 87, No. 6, pp. 2016-2022.

Witte et al., "Experimental Heart Failure in Rats: Effects on Cardiovascular Circadian Rhythms and on Myocardial β-adrenergic Signaling," Cardiovascular Research, (Aug. 2000), vol. 47, No. 2, pp. 350-358.

Notification of Transmittal of Translation of the International Preliminary Report of Patentability (Forms PCT/IB/338 and PCT/IB/373) and the Written Opinion of the International Searching Authority (Form PCT/ISA/237) dated Feb. 1, 2018, by the International Bureau of WIPO in corresponding International Application No. PCT/EP2016/066891. (9 pages).

Fan, Yang et al., "Observation on the Antihypertensive Effect of Valsartan in Patients with Hypertension and Its Effect on Heart Rate," Hypertension Annual Conference Proceedings, 2005, Cardiology Department of People's Hospital, Shixing County, Guangdong Province (512500).

Pinto et al., "Lessons from rat models of hypertension: from Goldblatt to genetic engineering," Cardiovascular Research 1998(39):77-88.

Engler et al.,"The TGR(mRen2)27 Transgenic Rat Model of Hypertension," Regulatory Peptides 1998;77:3-8.

Khosrow Tayebati et al., "Spontaneously hypertensive rat as a model of vascular brain disorder: microanatomy, neurochemistry and behavior" J Neurol Sci Nov. 15, 2012;322(1-2):241-9.

Hultstroem, "Development of structural kidney damage in spontaneously hypertensive rats" J Hypertension Jun. 2012;30(6):1087-1091.

Mullins et al., "Renal Disease Pathophysiology and Treatment: Contributions from the Rat," Disease Models & Mechanisms 2016;9:1419-1433.

Kovacs et al., "Renin Overexpression Leads to Increased Titin-Based Stiffness Contributing to Diastolic Dysfunction in Hypertensive mRen2 Rats," Am J Physiol Heart Circ Physiol 2016;310: H1671-H1682.

Messerli et al., "Essential Hypertension," Lancet 2007; 370: 591-603.

* cited by examiner

STIMULATORS AND/OR ACTIVATORS OF SOLUBLE GUANYLATE CYCLASE (SGC) IN COMBINATION WITH AN INHIBITOR OF NEUTRAL ENDOPEPTIDASE (NEP INHIBITOR) AND/OR AN ANGIOTENSIN AII ANTAGONIST AND THE USE THEREOF

The present invention relates to stimulators and/or activators of soluble guanylate cyclase in combination with an inhibitor of neutral endopeptidase and/or angiotensin AII antagonists and the use thereof for the treatment and/or prophylaxis of cardiovascular disorders, for example heart failure with preserved ejection fraction or heart failure with reduced ejection fraction, renal disorders, for example chronic kidney failure, urological disorders, lung disorders, disorders of the central nervous system, for regulation of cerebral perfusion, for example in the event of vascular cerebral states of dementia, for the treatment and/or prophylaxis of fibrotic disorders and other disease symptoms (e.g. end organ damage affecting the brain, kidney or heart).

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family known to date can be classified into two groups either by structural features or by the type of ligands: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory center. This is of central importance for the activation mechanism. NO is able to bind to the iron atom of heme and thus markedly increase the activity of the enzyme. Heme-free preparations cannot, by contrast, be stimulated by NO. Carbon monoxide (CO) is also able to bind to the central iron atom of heme, but the stimulation by CO is much less than that by NO. The particulate membrane-bound guanylate cyclases consist of the cytosolic catalytic domain, a transmembrane region and the extracellular ligand-binding domain. The binding of natriuretic peptides to the extracellular ligand-binding domain leads to the activation of the catalytic domain and the biosynthesis of cGMP from GTP. Neutral endopeptidase (neprilysin) inactivates natriuretic peptides by proteolytic cleavage and consequently has an inhibiting effect on the particulate guanylate cyclase.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, arteriosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has been made predominantly of compounds such as organic nitrates whose effect is based on direct release of NO. The latter is formed by bioconversion and activates soluble guanylate cyclase by attacking the central iron atom of heme. In addition to the side effects, the development of tolerance is one of the crucial disadvantages of this mode of treatment.

By means of sGC activators and stimulators, the native as well as the heme-free form of soluble guanylate cyclase are directly activated or stimulated.

Using sGC activators, it is also possible to directly stimulate oxidized forms of soluble guanylate cyclase, and ultimately the heme-free form of sGC, independently of NO. This oxidized/heme-free form may accumulate in relatively high concentrations in tissue exposed to oxidative stress, so that, by using sGC activators, there should also be a targeted treatment of tissue under oxidative stress.

LCZ696 is an ARNI (angiotensin receptor neprilysin inhibitor) and therefore a dual active ingredient consisting of the angiotensin AII antagonist valsartan and the neprilysin inhibitor sacubitril. By means of neprilysin inhibition, reduced degradation of natriuretic peptides is achieved. These have in particular a diuretic and natriuretic effect due to their vasodilatory effects on preglomerular vessels. In addition, they can also inhibit sodium resorption in proximal tubule sections.

The combination of angiotensin receptor blockade and neprilysin inhibition by LCZ696 (a combination of the angiotensin receptor antagonist valsartan and the NEP inhibitor sacubitril) was recently investigated in clinical trials (phase III) in patients with heart failure and resulted in a reduction in the risk of death and hospitalization (McMurray et al 2014 NEJM). In addition to the desired increase in ANP and cGMP, a compensatory increase in renin and angiotensin was measured on LCZ696 administration both in healthy subjects and in hypertensive patients (Gu J. et al J Clin Pharmacol. 2010 April; 50(4):401-14).

A disadvantage of the administration of LCZ696 for reducing blood pressure is that compensatory effects of the heart rate, such as, for example, a reflex tachycardia with accompanying blood pressure reduction can be observed.

Accordingly, the object of the present invention is to provide combinations of pharmaceutical active ingredients for the treatment of cardiovascular disorders which reduce the mean arterial blood pressure and have as little as possible or no effect on hemodynamic parameters such as heart rate. This is intended to overcome the disadvantages described above, the compensatory effects of the heart rate, which are associated with a reduction in blood pressure.

In order to achieve this object, sGC stimulators and/or sGC activators in combination with neprilysin inhibitors and/or angiotensin AII antagonists were investigated under acute and, in particular, under chronic use, with the assumption that under experimental conditions positive effects on blood pressure and heart rate can be shown which are caused by the resulting plasma and tissue cGMP levels. These experimental conditions consist of healthy animals or also animals with hypertension (e.g. spontaneously hypertensive rats). In this case, the experiments are conducted with sGC stimulators and/or activators "head-to-head" against the sole combination of neprilysin inhibitors and angiotensin AII antagonists, such as, for example, LCZ696.

These experiments are intended to determine whether the enhancement of cGMP by stimulating the soluble guanylate cyclase with sGC stimulators and/or activators in combination with sacubitril (activation of the particulate, membranedependent guanylate cyclase by inhibition of neprilysin) and/or an angiotensin AII antagonist has an advantageous effect on, for example, hemodynamic parameters such as heart rate and mean arterial blood pressure.

The solution to the object stated above and the subject matter of the present invention are the following combinations of sGC stimulators and/or sGC activators with neprilysin inhibitors and/or angiotensin AII antagonists.

The combination of stimulators and/or activators of soluble guanylate cyclase with a neprilysin inhibitor and/or an angiotensin AII antagonist leads to vessel relaxation and/or controllable reduction in blood pressure. The combination is therefore suitable for the treatment and/or prophylaxis of diseases, preferably cardiovascular disorders, particularly for the treatment and/or prophylaxis of heart failure with preserved ejection fraction or heart failure with reduced ejection fraction, renal disorders, lung disorders, and for the treatment and/or fibrotic disorders in humans and animals.

Angiotensin AII antagonists of the combinations according to the present invention administered are, by way of example and preferably, valsartan, losartan, candesartan, telmisartan, irbesartan, olmesartan, eprosartan or azilsartan and preferably valsartan.

Valsartan is the angiotensin AII antagonist (S)—N-(1-carboxy-2-methylprop-1-yl)-N-pentanoyl-N-[2'-(1H-tetrazol-5-yl)biphenyl-4-ylmethyl]amine of the formula (30)

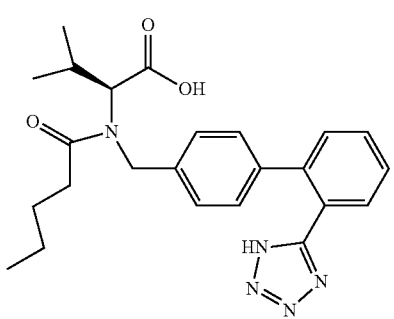

(30)

or a salt, solvate or solvate of the salts thereof and has been described in EP 0 443 983 A and U.S. Pat. No. 5,399,578 A.

The NEP inhibitor of the combinations according to the present invention is N-(3-carboxy-1-oxopropyl)-(4S)-(p-phenylphenylmethyl)-4-amino-2R-methylbutanoic acid of the formula (31)

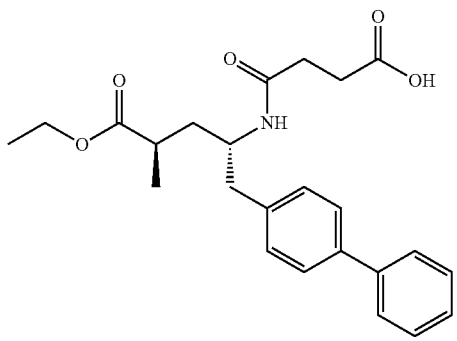

(31)

or an ester of the acid or in each case a salt, solvate or solvate of the salts of the acid or ester. Acid and ester of the NEP inhibitor of the combinations according to the present invention are described in EP 0 555 175 A1.

A preferred form of N-(3-carboxy-1-oxopropyl)-(4S)-(p-phenylphenylmethyl)-4-amino-2R-methylbutanoic acid is in the form of the ethyl ester, ethyl N-(3-carboxy-1-oxopropyl)-(4S)-(p-phenylphenylmethyl)-4-amino-2R-methylbutanoate.

With respect to ethyl N-(3-carboxy-1-oxopropyl)-(4S)-(p-phenylphenylmethyl)-4-amino-2R-methylbutanoate, preferred salts include the sodium salt, the triethanolamine salt and the tris(hydroxymethyl)aminomethane salt.

In the combinations according to the invention, valsartan and the NEP inhibitor may be present in each case individually or as trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate.

The trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate complex, also known as LCZ696, is described in more detail in EP 1 948 158 A1.

sGC stimulators and activators in the context of the combinations according to the present invention are the compounds disclosed in the following published specifications: WO03/097063, WO03/09545, WO04/009589, WO03/004503, WO02/070462, WO2007/045366, WO2007/045369, WO2007/045370, WO2007/045433, WO2007/045367, WO2007/124854, WO2007/128454, WO2008/031513, WO2008/061657, WO2008/119457, WO2008/119458, WO2009/127338, WO2010/079120, WO2010/102717, WO2011/051165, WO2011/147809, WO2011/141409, WO2014/012935, WO2012/059549, WO2012/004259, WO2012/004258, WO2012/059548, WO2012/028647, WO2012/152630, WO2012/076466, WO2014/068099, WO2014/068104, WO2012/143510, WO2012/139888, WO2012/152629, WO2013/004785, WO2013/104598, WO2013/104597, WO2013/030288, WO2013/104703, WO2013/131923, WO2013/174736, WO2014/012934, WO2014/068095, WO2014/195333, WO2014/128109, WO2014/131760, WO2014/131741, WO2015/018808, WO2015/004105, WO2015/018814, WO98/16223, WO98/16507, WO98/23619, WO00/06569, WO01/19776, WO01/19780, WO01/19778, WO02/042299, WO02/092596, WO02/042300, WO02/042301, WO02/036120, WO02/042302, WO02/070459, WO02/070460, WO02/070461, WO02/070510, WO2012/165399, WO2014/084312, WO2011/115804, WO2012/003405, WO2012/064559, WO2014/047111, WO2014/047325, WO2011/149921, WO2010/065275, WO2011/119518, WO2015/08885, WO2015/08886, WO2014/144100.

Preferred sGC stimulators and activators in the context of the combinations according to the present invention are
2-[1-(2-fluorobenzyl)-1H-pyrazolo[3,4-b]pyridin-3-yl]-5-(4-morpholinyl)-4,6-pyrimidinediamine (1), disclosed as example 16 in WO 00/06569,
2-[1-(2-fluorobenzyl)-1H-pyrazolo[3,4-b]pyridin-3-yl]-5-(4-pyridinyl)-4-pyrimidineamine (2), disclosed as example 1 in WO 02/42301,
methyl 4,6-diamino-2-[1-(2-fluorobenzyl)-1H-pyrazolo[3,4-b]pyridin-3-yl]-5-pyrimidinyl(methyl)carbamate (3), disclosed as example 8 in WO 03/095451, methyl 4,6-diamino-2-[1-(2-fluorobenzyl)-1H-pyrazolo[3,4-b]pyridin-3-yl]-5-pyrimidinylcarbamate (4), disclosed as example 5 in WO 03/095451, 4-({(4-carboxybutyl)[2-(2-{[4-(2-phenylethyl)benzyl]oxy}phenyl)ethyl]amino}methyl)carboxylic acid (5), disclosed as example 8a in WO 01/019780, methyl {4,6-diamino-2-[5-fluoro-1-(2-fluorobenzyl)-1H-pyrazolo[3,4-b]pyridine-3-yl]pyrimidin-5-yl}carbamate (6), methyl {4,6-diamino-2-[5-fluoro-1-(2-fluorobenzyl)-1H-pyrazolo[3,4-b]pyridine-3-yl]pyrimidin-5-yl}methylcarbamate (7), methyl {4,6-diamino-2-[5-fluoro-1-(2-fluorobenzyl)-1H-pyrazolo[3,4-b]pyridin-3-yl]pyrimidin-5-yl}(2,2,2-trifluoroethyl)carbamate (8), disclosed in WO 2011/147809, 5-chloro-2-(5-chlorothiophene-2-sulfonylamino-N-(4-(morpholine-4-sulfonyl)phenyl)benzamide as sodium salt (9), disclosed in WO00/02851, 2-(4-chlorophenylsulfonylamino)-4,5-dimethoxy-N-(4-(thiomorpholine-4-sulfonyl)phenyl)benzamide (10), disclosed in WO00/02851, 1-{6-[5-chloro-2-({4-trans-4-}trifluoromethyl)cyclohexyl]benzyl}oxy)phenyl]pyridin-2-yl}-5-(trifluoromethyl)-1H-pyrazole-4-carboxylic acid (11), disclosed in WO 2009/032249, 1-[6-(2-(2-methyl-4-(trifluoromethoxyphenyl)benzyloxy)phenyl)pyridin-2-yl]-5-trifluoromethylpyrazole-4-carboxylic acid (12), disclosed in WO 2009/071504, 1[6-(3,4-dichlorophenyl)-2-pyridinyl-5-(trifluoromethyl)-1H-pyrazole-4-carboxylic acid (13), disclosed in WO 2009/068652, 1-({2-[3-chloro-5-(trifluoromethyl)phenyl]-5-methyl-1,3-thiazol-4-yl}methyl)-1H-pyrazole-4-carboxylic acid (14), 4-({2-[3-(trifluoromethyl)phenyl]-1,3-thiazol-4-yl}methyl)benzoic acid (15) and 1-({2-[2-fluoro-3-(trifluoromethyl)phenyl]-5-methyl-1,3-thiazol-4-yl}methyl)-1H-pyrazole-4-carboxylic acid (16) disclosed in WO 2009/123316, 4-amino-2-[5-chloro-3(3,3,3-trifluoropropyl)-1H-indazol-1-yl]-5,5-dimethyl-5,7-dihydro-6H-pyrrolo[2,3-d]pyrimidin-6-one (17), 4-amino-2[5-chloro-3-(2,3,6-trifluorobenzyl)-1H-indazol-1-yl]-5,5-dimethyl-5,7-dihydro-6H-pyrrolo[2,3-d]pyrimidin-6-one (18), 4-amino-5,5-dimethyl-2-[3-(2,3,6-trifluorobenzyl)1H-thieno[3,4-c]pyrazol-1-yl]-5,7-dihydro-6H-pyrrolo[2,3-d]pyrimidin-6-one (19), 4-amino-5,5-dimethyl-2-[3-(2,3,6-trifluorobenzyl)-1H-thieno[2,3-d]pyrazol-1-yl]-5,5-dimethyl-5,7-dihydro-6H-pyrrolo[2,3-d]pyrimidin-6-one (20), 4-amino-5,5-dimethyl-2-[7-(2,3,6-trifluorobenzyl)imidazo[1,5-b]pyridazin-5-yl]-5,7-dihydro-6H-pyrrolo[2,3-d]pyrimidin-6-one (21), 4-amino-2-[6-chloro-3-(2,3,6-trifluorobenzyl)imidazo[1,5-a]pyridin-1-yl]]-5,5-dimethyl-5,7-dihydro-6H-pyrrolo[2,3-d]pyrimidin-6-one (22), 4-amino-2-[6-fluoro-3-(2,3,6-trifluorobenzyl)imidazo[1,5-a]pyridin-1-yl]]-5,5-dimethyl-5,7-dihydro-6H-pyrrolo[2,3-d]pyrimidin-6-one (23), 4-amino-2-[6-fluoro-3-(2,3,6-trifluorobenzyl)6-fluoroimidazo[1,5-a]pyridin-1-yl]-5,5-dimethyl-5,7-dihydro-6H-pyrrolo[2,3-d]pyrimidin-6-one (24), 4-amino-5,5-dimethyl-2-[3-(2,4,6-trifluorobenzyl)imidazo[1,5-a]pyridin-1-yl]]-5,7-dihydro-6H-pyrrolo[2,3-d]pyrimidin-6-one (25), 4-amino-2-[3-(2-cyclopentylethyl)imidazo[1,5-a]pyridin-1-yl]-5,5-dimethyl-5,7-dihydro-6H-pyrrolo[2,3-d]pyrimidin-6-one (26), disclosed in WO 2010/065275, 3-(4-amino-5-cyclopropylpyrimidin-2-yl)-1-(2-fluorobenzyl)-1H-pyrazolo[3,4-b]pyridine (27), known as BAY 41-2272 disclosed as example 1 in WO 00/06568, 2-{5-fluoro-1-[(3-fluoropyridin-2-yl)methyl]-1H-pyrazolo[3,4-b]pyridin-3-yl}-5-methyl-5-(trifluoromethyl)-4-[(3,3,3-trifluoropropyl)amino]-5,7-dihydro-6H-pyrrolo[2,3-d]pyrimidin-6-one (28), disclosed as example 1 in WO 2014/131760, 3-(4-chloro-3-{[(2S,3R)-2-(4-chlorophenyl)-4,4,4-trifluoro-3-methylbutanoyl]amino}phenyl)-3-cyclopropylpropanoic acid (29) disclosed as example 22 in WO 2012/139888, 5-{[2-(4-carboxyphenyl)ethyl][2-(2-{[3-chloro-4'-(trifluoromethyl)biphenyl-4-yl]methoxy}phenyl)ethyl]amino}-5,6,7,8-tetrahydroquinoline-2-carboxylic acid formula (32) and 5-{(4-carboxybutyl)[2-(2-{[3-chloro-4'-(trifluoromethyl)biphenyl-4-yl]methoxy}phenyl)ethyl]amino}-5,6,7,8-tetrahydroquinoline-2-carboxylic acid of the formula (33) are disclosed as examples in WO 2014/012934, ent-N-[(2S)-amino-2-methylbutyl]-8-[(2,6-difluorobenzyl)oxy]-2,6-dimethylimidazo[1,2-a]pyridine-3-carboxamide (enantiomer A) of the formula (34), ent-N-(2-amino-2-methylbutyl)-8-[(2,6-difluorobenzypoxy]-2,6-dimethylimidazo[1,2-a]pyridine-3-carboxamide (enantiomer B) of the formula (35), ent-N-(2-amino-5,5,5-trifluoro-2-methylpentyl)-2,6-dimethyl-8-[(2,3,6-trifluorobenzyl)oxy]imidazo[1,2-a]pyridine-3-carboxamide (enantiomer B) of the formula (36), ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer B) of the formula (37), ent-N-(2-amino-5,5,5-trifluoro-2-methylpentyl)-8-[(2,6-difluorobenzyl)oxy]-2,6-dimethylimidazo[1,2-a]pyridine-3-carboxamide (enantiomer A) of the formula (38), ent-N-(2-amino-3-fluoro-2-methylpropyl)-2,6-dimethyl-8-[(2,3,6-trifluorobenzyl)oxy]imidazo[1,2-a]pyridine-3-carboxamide (enantiomer B) of the formula (39), ent-N-(2-amino-3-fluoro-2-methylpropyl)-8-[(2,6-difluorobenzyl)oxy]-2,6-dimethylimidazo[1,2-a]pyridine-3-carboxamide (enantiomer B) of the formula (40), ent-N-(2-amino-3-fluoro-2-methylpropyl)-8-[(2,6-difluorobenzyl)oxy]-2,6-dimethylimidazo[1,2-a]pyridine-3-carboxamide (enantiomer A) of the formula (41), rac-N-(2-amino-3-fluoro-2-methylpropyl)-8-[(2,6-difluorobenzyl)oxy]-2,6-dimethylimidazo[1,2-a]pyridine-3-carboxamide formate of the formula (42), ent-N-(2-amino-3-fluoro-2-methylpropyl)-2,6-dimethyl-8-[(2,3,6-trifluorobenzyl)oxy]imidazo[1,2-a]pyridine-3-carboxamide (enantiomer A) of the formula (43), ent-N-(2-amino-3-fluoro-2-methylpropyl)-8-[(2,6-difluorobenzyl)oxy]-6-(difluoromethyl)-2-methylimidazo[1,2-a]pyridine-3-carboxamide (enantiomer B) of the formula (44), ent-N-(2-amino-3-fluoro-2-methylpropyl)-8-[(2,6-difluorobenzypoxy]-6-(difluoromethyl)-2-methylimidazo[1,2-a]pyridine-3-carboxamide (enantiomer A) of the formula (45), ent-N-(2-amino-3-fluoro-2-methylpropyl)-8-[(2,6-difluorobenzyl)oxy]-6-(fluoromethyl)-2-methylimidazo[1,2-a]pyridine-3-carboxamide of the formula (46) are disclosed as examples in WO 2014/068099.

(1)
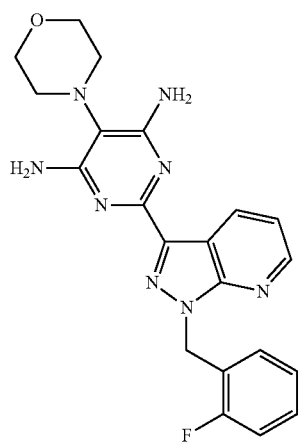
(2)
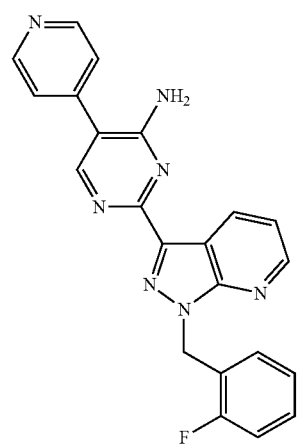
(3)
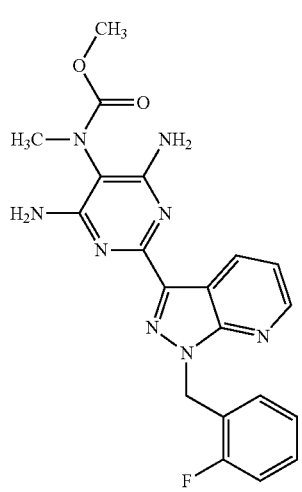
(4)
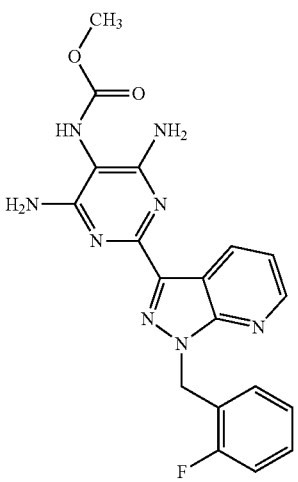
(5)
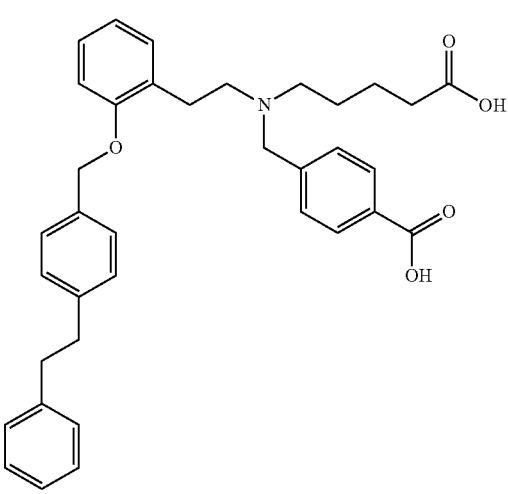
(6)
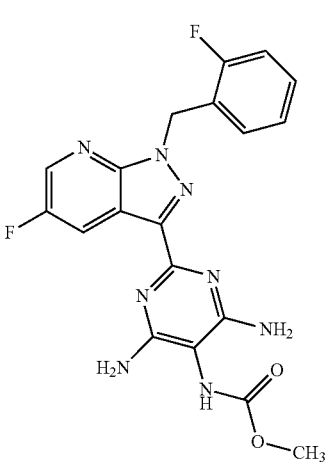

(7)
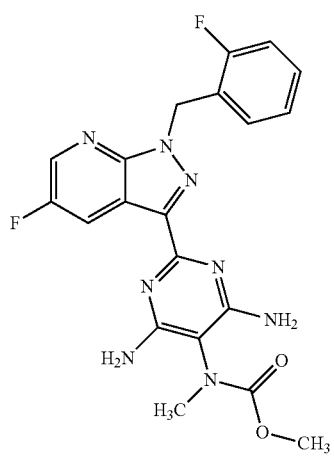
(8)
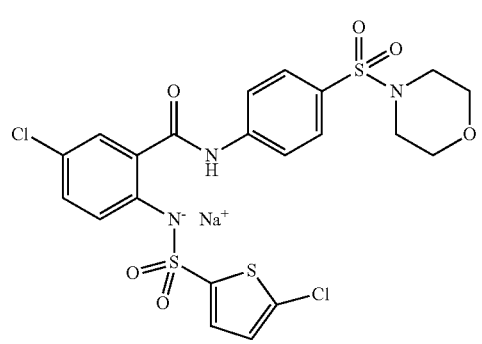
(9)
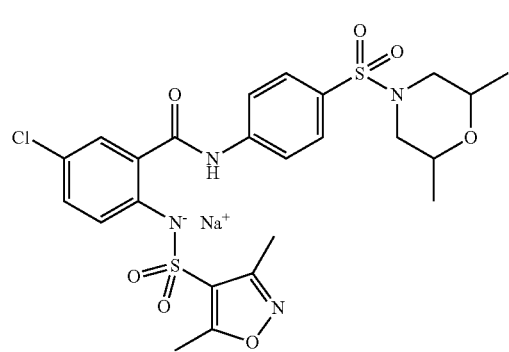
(10)
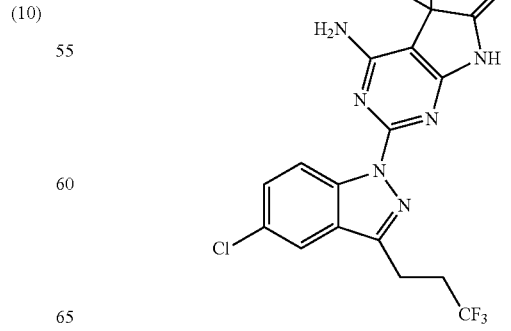
(11)
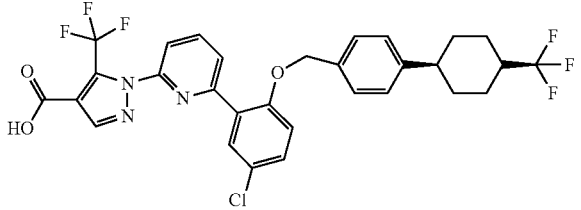
(12)
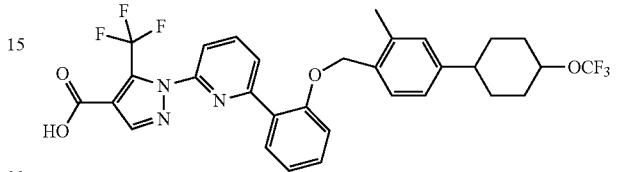
(13)
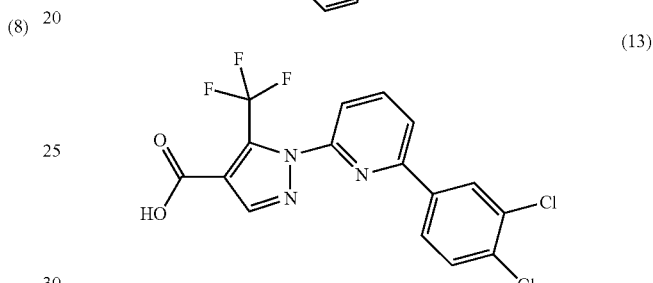
(14)
(15)
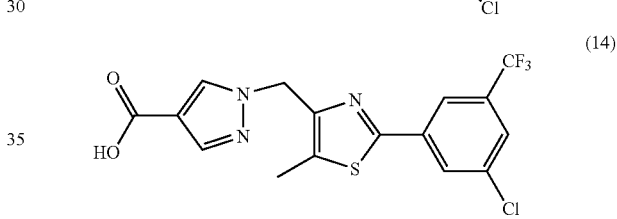
(16)
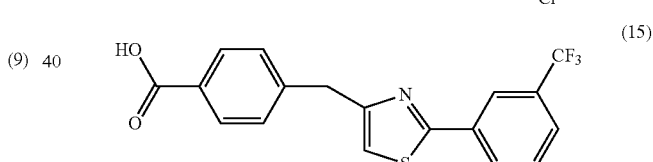
(17)
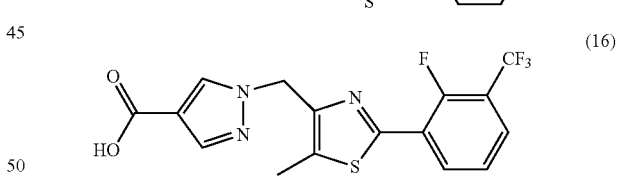

11
-continued
(18)
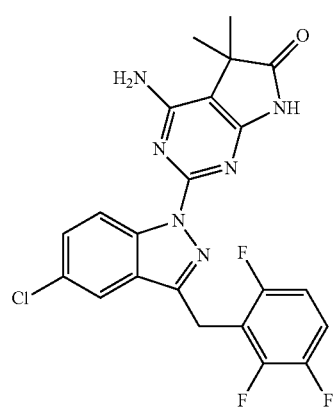
(19)
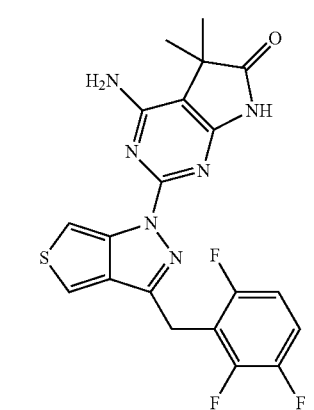
(20)
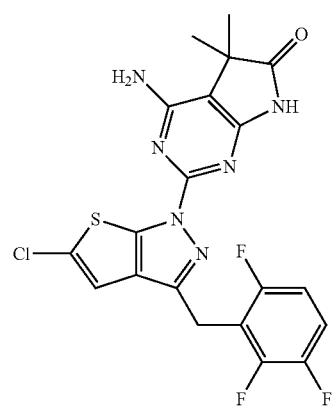
(21)
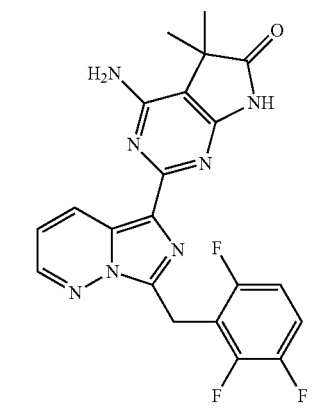
12
-continued
(22)
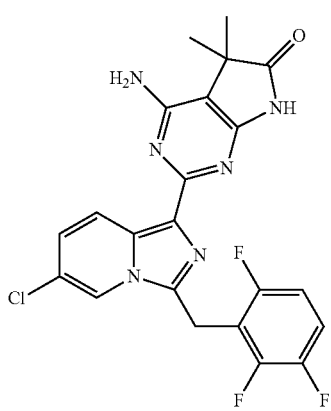
(23)
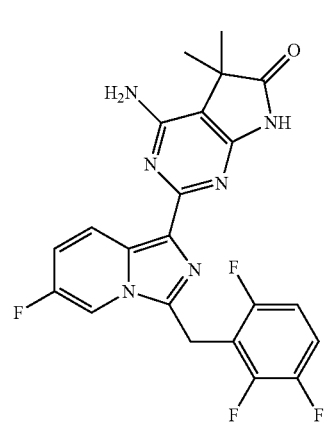
(24)
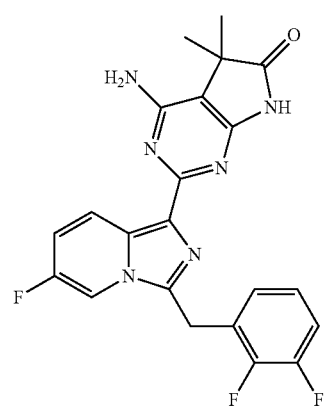
(25)
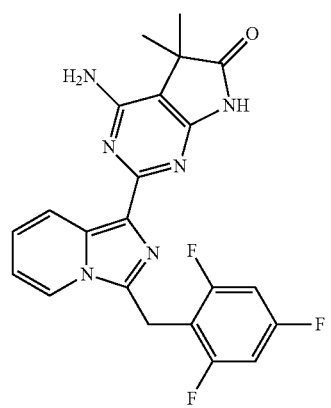

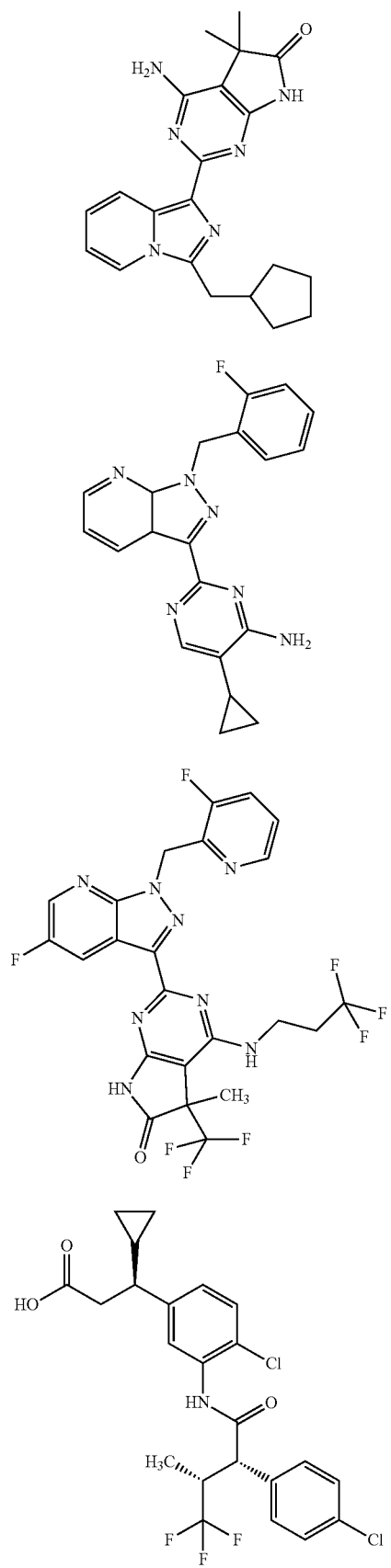

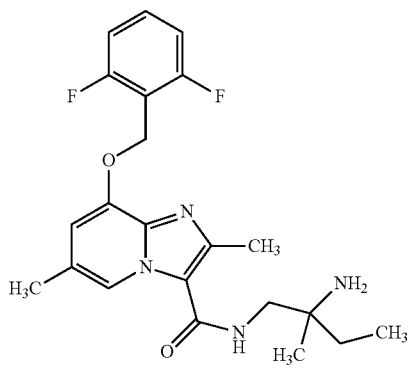
(35)
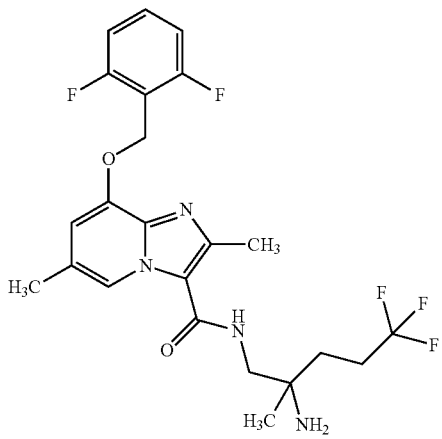
(38)
(36)
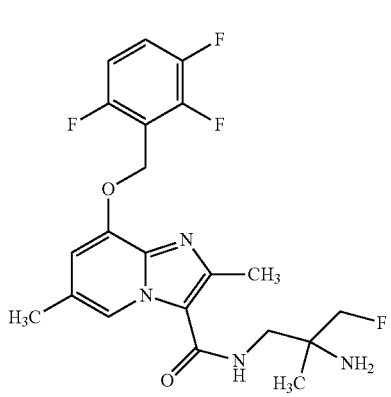
(39)
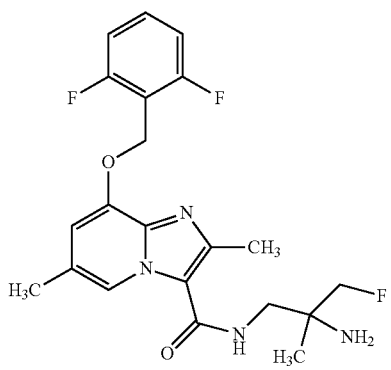
(40)
(37)
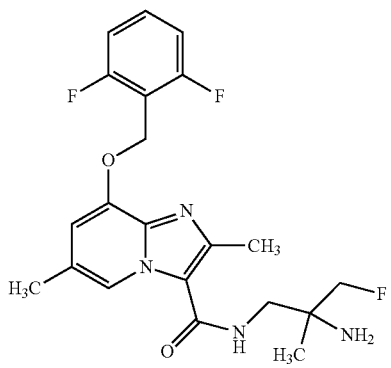
(41)

-continued

(42)
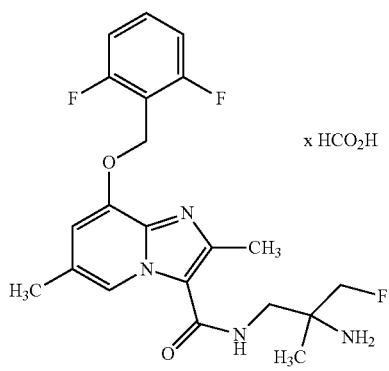
x HCO₂H

(43)
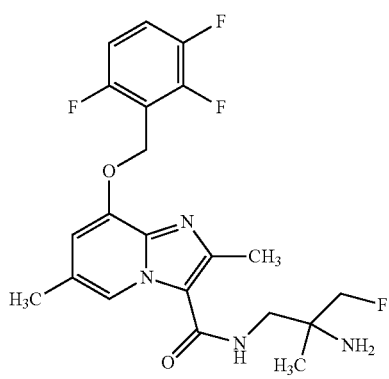

(44)
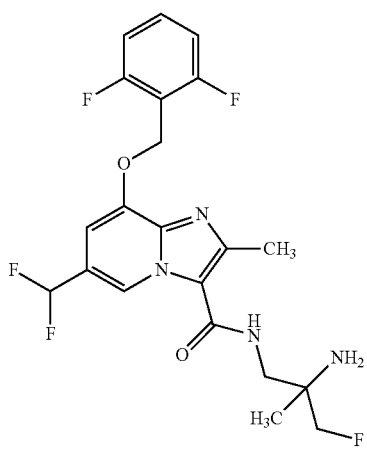

(45)
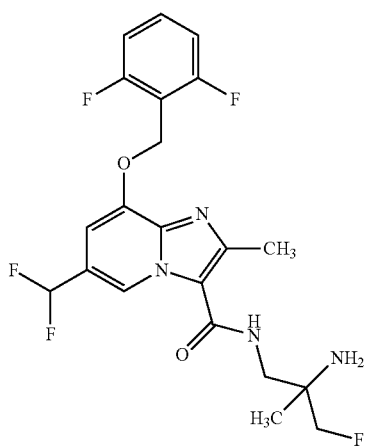

-continued

(46)
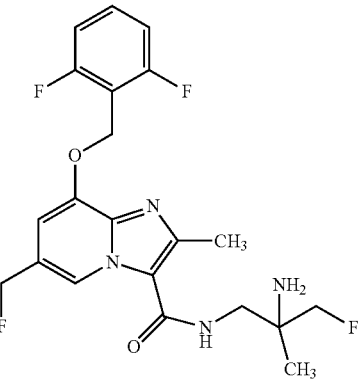

Compounds of the formulae (1), (2), (3), (4), (6)-(8), (17)-(27) and (34)-(46) are known as sGC stimulators.

Compounds of the formulae (5) and (9)-(16), (29), (32) and (33) are known as sGC activators.

In the context of the combinations according to the invention, preference is given to sGC stimulators of the formulae (1), (2), (3), (4), (6)-(8) and (17)-(27) and activators of the formulae (5) and (9)-(16) and (29).

In the context of the combinations according to the invention, preferred sGC stimulators are compounds of the formulae (1), (2), (3), (4), (6), (7), (27) and (28).

In the context of the combinations according to the invention, particularly preferred are the sGC stimulators of the formulae (3), (4), (6), (7) and (28).

In the context of the combinations according to the invention, particularly preferred are the sGC stimulators of the formulae (3) and (6).

In the context of the combinations according to the invention, particularly preferred is the sGC stimulator of the formula (6).

Particularly preferred in the context of the combinations according to the invention is the sGC activator of the formula (29).

The combinations according to the invention allow an effective treatment of cardiovascular diseases by reducing the mean arterial blood pressure and, as far as possible, no or little effects on the hemodynamic parameters, such as the heart rate, occur. Therefore, the disadvantages described above of the therapy forms known in the prior art, such as, for example, compensatory effects of the heart rate with accompanying blood pressure reduction, could be overcome.

Moreover, the combinations according to the invention show an unforeseeable, valuable pharmacological and pharmacokinetic spectrum of activity.

The combinations according to the invention are suitable for the prophylaxis and/or treatment of diseases due to their vessel-relaxing effect (vasorelaxation) and inhibition of platelet aggregation and lead to a decrease in blood pressure and to a rise in the coronary blood flow. These effects are mediated by stimulation of the soluble and/or particulate guanylate cyclase and/or blockade of the angiotensin receptor. In addition, the combinations according to the invention enhance the action of substances which increase the cGMP level, for example EDRF (endothelium-derived relaxing factor), NO donors, protoporphyrin IX, arachidonic acid or phenylhydrazine derivatives.

The present invention further relates to the use of sGC activators and/or sGC stimulators in combination with neprilysin inhibitors and/or angiotensin AII antagonists for the treatment of cardiovascular disorders, for example heart failure with preserved ejection fraction or heart failure with reduced ejection fraction, renal disorders, for example chronic kidney failure, urological disorders, lung disorders, disorders of the central nervous system, for regulation of cerebral perfusion, for example in the event of vascular cerebral states of dementia, for the treatment and/or prophylaxis of fibrotic disorders and other disease symptoms (e.g. end organ damage affecting the brain, kidney or heart).

The present invention further relates to sGC activators and/or sGC stimulators in combination with angiotensin AII antagonists and also the use thereof for the treatment of cardiovascular disorders, for example heart failure with preserved ejection fraction or heart failure with reduced ejection fraction, renal disorders, for example chronic kidney failure, urological disorders, lung disorders, disorders of the central nervous system, for regulation of cerebral perfusion, for example in the event of vascular cerebral states of dementia, for the treatment and/or prophylaxis of fibrotic disorders and other disease symptoms (e.g. end organ damage affecting the brain, kidney or heart).

By way of preference, the invention relates to administration of sGC stimulators and/or activators in combination with a neprilysin inhibitor such as, for example and with preference sacubitril and/or an angiotensin AII antagonist such as, for example and with preference valsartan, losartan, candesartan, telmisartan, irbesartan, olmesartan, eprosartan or azilsartan.

By way of preference, the present invention relates to combinations comprising an sGC stimulator and/or sGC activator, N-(3-carboxy-1-oxopropyl)-(4S)-(p-phenylphenylmethyl)-4-amino-2R-methylbutanoic acid or an ester thereof and/or valsartan and in each case the salts, solvates and solvates of the salts of an sGC stimulator and/or sGC activator, N-(3-carboxy-1-oxopropyl)-(4S)-(p-phenylphenylmethyl)-4-amino-2R-methylbutanoic acid or an ester thereof and/or valsartan.

The present invention further relates to combinations comprising an sGC stimulator and/or sGC activator and LCZ696 and also in each case the salts, solvates and solvates of the salts thereof.

The present invention particularly preferably relates to combinations comprising an sGC stimulator, sacubitril and/or an angiotensin AII antagonist and also in each case the salts, solvates and solvates of the salts thereof.

The present invention furthermore particularly preferably relates to combinations comprising an sGC stimulator, sacubitril and/or valsartan and also in each case the salts, solvates and solvates of the salts thereof.

The present invention furthermore particularly preferably relates to combinations comprising an sGC stimulator and LCZ696 and also in each case the salts, solvates and solvates of the salts thereof.

The present invention furthermore particularly preferably relates to combinations comprising the compound of the formula (6), N-(3-carboxy-1-oxopropyl)-(4S)-(p-phenylphenylmethyl)-4-amino-2R-methylbutanoic acid or an ester thereof and/or valsartan, and in each case the salts, solvates and solvates of the salts of the compound of the formula (6) and N-(3-carboxy-1-oxopropyl)-(4S)-(p-phenylphenylmethyl)-4-amino-2R-methylbutanoic acid or an ester thereof and/or valsartan.

The present invention furthermore particularly preferably relates to combinations comprising the compound of the formula (6) and LCZ696 and also in each case the salts, solvates and solvates of the salts thereof.

The present invention further relates to combinations comprising an sGC stimulator and/or sGC activator and valsartan, and also in each case the salts, solvates and solvates of the salts of an sGC stimulator and/or sGC activator and valsartan.

The present invention further relates to combinations comprising the compound of the formula (6) and valsartan, and also in each case the salts, solvates and solvates of the salts of the compound of the formula (6) and valsartan.

The components to be combined may be present as salts. Preferred salts in the context of the present invention are physiologically acceptable salts of the compounds to be combined. Also included are salts which are not themselves suitable for pharmaceutical applications but can be used, for example, for isolation or purification of the compounds to be combined.

The present invention further relates to combinations in which the molar ratio of the compound of the formula (6) to valsartan to N-(3-carboxy-1-oxopropyl)-(4S)-(p-phenylphenylmethyl)-4-amino-2R-methylbutanoic acid or an ester thereof is 0.01-1:1:1.

The present invention further relates to combinations in which the molar ratio of the compound of the formula (6) to trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate is 0.01-1:1.

The present invention further relates to combinations in which the molar ratio of the compound of the formula (6) to N-(3-carboxy-1-oxopropyl)-(4S)-(p-phenylphenylmethyl)-4-amino-2R-methylbutanoic acid or an ester thereof is 0.01-1:1.

The present invention further relates to combinations in which the molar ratio of the compound of the formula (6) to valsartan is 0.01-1:1.

The present invention further relates to combinations according to the invention for the treatment and/or prophylaxis of diseases, wherein the compound of the formula (6) is administered once daily and valsartan and ethyl N-(3-carboxy-1-oxopropyl)-(4S)-(p-phenylphenylmethyl)-4-amino-2R-methylbutanoate or N-(3-carboxy-1-oxopropyl)-(4S)-(p-phenylphenylmethyl)-4-amino-2R-methylbutanoic acid or an ester thereof are administered twice daily.

The present invention further relates to combinations according to the invention for the treatment and/or prophylaxis of diseases, wherein 1.25-20 mg of the compound of the formula (6), 20-200 mg of valsartan and 20-200 mg of N-(3-carboxy-1-oxopropyl)-(4S)-(p-phenylphenylmethyl)-4-amino-2R-methylbutanoic acid or an ester thereof are administered.

The present invention further relates to combinations according to the invention for the treatment and/or prophylaxis of diseases, wherein 1.25-20 mg of the compound of the formula (6) and 20-200 mg of N-(3-carboxy-1-oxopropyl)-(4S)-(p-phenylphenylmethyl)-4-amino-2R-methylbutanoic acid or an ester thereof are administered.

The present invention further relates to combinations according to the invention for the treatment and/or prophylaxis of diseases, wherein 1.25-20 mg of the compound of the formula (6) and 20-200 mg of valsartan are administered.

The present invention further relates to combinations according to the invention for the treatment and/or prophylaxis of diseases, wherein the compound of the formula (6) is administered once daily and trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5- ylate)biphenyl-4'-ylmethyl}amino)butyrate] hemipentahydrate is administered twice daily.

The present invention further relates to combinations according to the invention for the treatment and/or prophylaxis of diseases, wherein 1.25-20 mg of the compound of the formula (6) and 40-400 mg of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate are administered.

The present invention further relates to combinations according to the invention, wherein the molar ratio of the compound of the formula (6) to valsartan to N-(3-carboxy-1-oxopropyl)-(4S)-(p-phenylphenylmethyl)-4-amino-2R-methylbutanoic acid or an ester thereof is 0.001-1:1:3, 0.001-1:3:1, 0.001-1:1:2, 0.001-1:2:1 or 0.001-1:1:1, preferably 0.005-0.75:1:3, 0.005-0.75:3:1, 0.005-0.75:1:2, 0.005-0.75:2:1 or 0.005-0.75:1:1 and most preferably 0.01-0.5:1:1.

The present invention further relates to combinations according to the invention, wherein the molar ratio of the compound of the formula (6) to trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is 0.001-1:1, preferably 0.005-0.75:1 and most preferably 0.01-0.5:1.

The present invention further relates to combinations comprising the compound of the formula (29), N-(3-carboxy-1-oxopropyl)-(4S)-(p-phenylphenylmethyl)-4-amino-2R-methylbutanoic acid or the esters thereof and/or valsartan, and also in each case the salts, solvates and solvates of the salts of the compound of the formula (29), N-(3-carboxy-1-oxopropyl)-(4S)-(p-phenylphenylmethyl)-4-amino-2R-methylbutanoic acid or the esters thereof and/or valsartan.

The present invention further relates to combinations comprising the compound of the formula (29) and tri sodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate and also in each case the salts, solvates and solvates of the salts thereof.

The present invention further relates to combinations comprising the compound of the formula (29) and valsartan, and also in each case the salts, solvates and solvates of the salts of the compound of the formula (29) and valsartan.

The present invention further relates to combinations in which the molar ratio of the compound of the formula (29) to valsartan to N-(3-carboxy-1-oxopropyl)-(4S)-(p-phenylphenylmethyl)-4-amino-2R-methylbutanoic acid or the esters thereof is 0.02-1:1:1.

The present invention further relates to combinations in which the molar ratio of the compound of the formula (29) to trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is 0.02-1:1.

The present invention further relates to combinations in which the molar ratio of the compound of the formula (29) to N-(3-carboxy-1-oxopropyl)-(4S)-(p-phenylphenylmethyl)-4-amino-2R-methylbutanoic acid or the esters thereof is 0.02-1:1.

The present invention further relates to combinations in which the molar ratio of the compound of the formula (29) to valsartan is 0.02-1:1.

The present invention further relates to combinations according to the invention for the treatment and/or prophylaxis of diseases, wherein the compound of the formula (29) is administered once daily and valsartan and ethyl N-(3-carboxy-1-oxopropyl)-(4S)-(p-phenylphenylmethyl)-4-amino-2R-methylbutanoate or N-(3-carboxy-1-oxopropyl)-(4S)-(p-phenylphenylmethyl)-4-amino-2R-methylbutanoic acid are administered twice daily.

The present invention further relates to combinations according to the invention for the treatment and/or prophylaxis of diseases, wherein 2.5-20 mg of the compound of the formula (29), 20-200 mg of valsartan and 20-200 mg of N-(3-carboxy-1-oxopropyl)-(4S)-(p-phenylphenylmethyl)-4-amino-2R-methylbutanoic acid or the esters thereof are administered.

The present invention further relates to combinations according to the invention for the treatment and/or prophylaxis of diseases, wherein 2.5-20 mg of the compound of the formula (29) and 20-400 mg of N-(3-carboxy-1-oxopropyl)-(4S)-(p-phenylphenylmethyl)-4-amino-2R-methylbutanoic acid or the esters thereof are administered.

The present invention further relates to combinations according to the invention for the treatment and/or prophylaxis of diseases, wherein 2.5-20 mg of the compound of the formula (29), 20-400 mg of valsartan or the esters thereof are administered.

The present invention further relates to combinations according to the invention for the treatment and/or prophylaxis of diseases, wherein the compound of the formula (29) is administered once daily and trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is administered twice daily.

The present invention further relates to combinations according to the invention for the treatment and/or prophylaxis of diseases, wherein 2.5-20 mg of the compound of the formula (29) and 40-400 mg of trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate are administered.

The present invention further relates to combinations according to the invention, wherein the molar ratio of the compound of the formula (29) to valsartan to N-(3-carboxy-1-oxopropyl)-(4S)-(p-phenylphenylmethyl)-4-amino-2R-methylbutanoic acid or an ester thereof is 0.001-1:1:3, 0.001-1:3:1, 0.001-1:1:2, 0.001-1:2:1 or 0.001-1:1:1, preferably 0.005-0.75:1:3, 0.005-0.75:3:1, 0.005-0.75:1:2, 0.005-0.75:2:1 or 0.005-0.75:1:1 and most preferably 0.02-0.5:1:1.

The present invention further relates to combinations according to the invention, wherein the molar ratio of the compound of the formula (29) to trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate is 0.001-1:1, preferably 0.005-0.75:1 and most preferably 0.01-0.5:1.

The present invention further relates to combinations according to the invention for the treatment and/or prophylaxis of diseases.

The present invention further relates to combinations according to the invention for use in a method for the treatment and/or prophylaxis of cardiovascular disorders, renal disorders, lung disorders, and also for the treatment and/or prophylaxis of fibrotic disorders.

The present invention further relates to a medicament comprising at least one combination according to the invention in combination with an inert, non-toxic, pharmaceutically suitable excipient.

The present invention further relates to a medicament comprising at least one combination according to the invention in combination with one or more further active ingredients selected from the group consisting of ACE inhibitors, renin inhibitors, beta blockers, acetylsalicylic acid, diuretics, calcium antagonists, statins, digitalis (digoxin) derivatives, calcium sensitizers, nitrates and antithrombotics.

The present invention further relates to a medicament comprising at least one combination according to the invention for the treatment and/or prophylaxis of cardiovascular disorders, renal disorders, lung disorders, and also for the treatment and/or prophylaxis of fibrotic disorders.

The present invention further relates to a method for the treatment and/or prophylaxis of cardiovascular disorders, renal disorders, lung disorders, and also for the treatment and/or prophylaxis of fibrotic disorders, in humans and animals using at least one combination according to the invention.

The invention also relates to the combination of separate pharmaceutical compositions in kit form. This is a kit comprising two or three separate units: a pharmaceutical composition of an sGC stimulator and/or sGC activator, a pharmaceutical NEP inhibitor composition and/or a pharmaceutical valsartan composition.

The invention also relates to a preferred kit form comprising two units: a pharmaceutical composition comprising an sGC stimulator and/or sGC activator and a pharmaceutical composition comprising an NEP inhibitor and/or valsartan.

The invention also relates to a preferred kit form comprising two units: a pharmaceutical composition comprising an sGC stimulator and/or sGC activator and a pharmaceutical composition comprising LCZ696.

The invention also relates to a preferred kit form comprising two units: a pharmaceutical composition comprising the compound of the formula (6) and a pharmaceutical composition comprising LCZ696.

The invention also relates to a preferred kit form comprising two units: a pharmaceutical composition comprising the compound of the formula (29) and a pharmaceutical composition comprising LCZ696.

The kit is particularly advantageous if the separate components have to be administered in different dose forms or in different dose intervals.

The present invention further relates to a kit comprising a pharmaceutical composition comprising an sGC stimulator and/or sGC activator and a pharmaceutical composition comprising an angiotensin AII antagonist and N-(3-carboxy-1-oxopropyl)-(4S)-(p-phenylphenylmethyl)-4-amino-2R-methylbutanoic acid or the esters thereof.

The present invention further relates to a kit comprising a pharmaceutical composition comprising an sGC stimulator and/or sGC activator and a pharmaceutical composition comprising valsartan and N-(3-carboxy-1-oxopropyl)-(4S)-(p-phenylphenylmethyl)-4-amino-2R-methylbutanoic acid or the esters thereof.

The present invention further relates to a kit comprising a pharmaceutical composition comprising an sGC stimulator and/or sGC activator and a pharmaceutical composition comprising trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate.

The present invention further relates to a kit comprising a pharmaceutical composition comprising the compound of the formula (6) and a pharmaceutical composition comprising valsartan and N-(3-carboxy-1-oxopropyl)-(4S)-(p-phenylphenylmethyl)-4-amino-2R-methylbutanoic acid or the esters thereof.

The present invention further relates to a kit comprising a pharmaceutical composition comprising the compound of the formula (6) and a pharmaceutical composition comprising trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate.

The present invention further relates to a kit comprising a pharmaceutical composition comprising the compound of the formula (29) and a pharmaceutical composition comprising valsartan and N-(3-carboxy-1-oxopropyl)-(4S)-(p-phenylphenylmethyl)-4-amino-2R-methylbutanoic acid or the esters thereof.

The present invention further relates to a kit comprising a pharmaceutical composition comprising the compound of the formula (29) and a pharmaceutical composition comprising trisodium [3-((1S,3R)-1-biphenyl-4-ylmethyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate.

Accordingly, the combinations according to the invention can be used in medicaments for the treatment and/or prophylaxis of cardiovascular disorders such as, for example, elevated blood pressure (hypertension), resistant hypertension, acute and chronic heart failure, heart failure with preserved ejection fraction (HFpEF) or heart failure with reduced ejection fraction (HFrEF), coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation such as, for example, pulmonary edema, cerebral edema, renal edema or edema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of male erectile dysfunction and female sexual dysfunction.

In the context of the present invention, the term "heart failure" encompasses both acute and chronic manifestations of heart failure, and also more specific or related types of disease, such as acute decompensated heart failure, right heart failure, left heart failure, global failure, ischamic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure and acute phases of worsening of existing chronic heart failure (worsening heart failure).

In addition, the combinations according to the invention can also be used for the treatment and/or prophylaxis of arteriosclerosis, impaired lipid metabolism, hypolipoproteinemias, dyslipidemias, hypertriglyceridemias, hyperlipidemias, hypercholesterolemias, abetelipoproteinemia, sitosterolemia, xanthomatosis, Tangier disease, adiposity, obesity and of combined hyperlipidemias and metabolic syndrome.

The combinations according to the invention can also be used for the treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing. The combinations according to the invention are also suitable for the treatment of muscular dystrophy, such as Becker-Kiener muscular dystrophy (BMD) and Duchenne muscular dystrophy (DMD).

The combinations according to the invention are furthermore suitable for the treatment and/or prophylaxis of urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic over-active bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The combinations according to the invention are also suitable for the treatment and/or prophylaxis of kidney disorders, in particular of acute and chronic renal insufficiency and acute and chronic kidney failure. In the context of the present invention, the term "renal insufficiency" encompasses both acute and chronic manifestations of renal insufficiency, and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the combinations according to the invention for the treatment and/or prophylaxis of sequelae of renal insufficiency, for example pulmonary edema, heart failure, uremia, anemia, electrolyte disorders (for example hyperkalemia, hyponatremia) and disorders in bone and carbohydrate metabolism.

In addition, the combinations according to the invention are also suitable for the treatment and/or prophylaxis of asthmatic disorders, lung disorders such as pulmonary arterial hypertension (PAH) and other forms of pulmonary hypertension (PH) including left-heart disease-, HIV-, sickle cell anemia-, thromboembolism- (CTEPH), sarcoidosis-, COPD- or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF). In addition, the combinations mentioned according to the invention may be used as bronchodilators.

The combinations described in the present invention are also combinations for the treatment and/or prophylaxis of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeldt-Jakob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

In addition, the combinations according to the invention are also suitable for the regulation of cerebral perfusion and for example are effective agents for controlling vascular cerebral dementia and migraine. They are also suitable for the prophylaxis and control of sequelae of cerebral infarct (Apoplexia cerebri) such as stroke, cerebral ischemias and skull-brain trauma. The combinations according to the invention can likewise be used for controlling states of pain and tinnitus.

In addition, the combinations according to the invention have anti-inflammatory action and can therefore be used as anti-inflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin disorders and inflammatory eye disorders.

Furthermore, the combinations according to the invention may also be used for the treatment and/or prophylaxis of autoimmune diseases.

The combinations according to the invention may also be suitable for the treatment and/or prophylaxis of fibrotic disorders of the internal organs, for example the lung, the heart, the kidney, the skin, the bone marrow and in particular the liver, and also dermatological fibroses and fibrotic eye disorders. In the context of the present inventions, the term "fibrotic disorders" includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, systemic sclerosis, scleroderma, digital ulcerations, morphea, keloids, hypertrophic scarring (also following surgical procedures), nevi, diabetic retinopathy, proliferative vitroretinopathy and disorders of the connective tissue (for example sarcoidosis).

The combinations according to the invention are also suitable for controlling postoperative scarring, for example as a result of glaucoma operations.

The combinations according to the invention may also be used cosmetically for ageing and keratinizing skin.

Moreover, the combinations according to the invention are suitable for the treatment and/or prophylaxis of hepatitis, neoplasms, osteoporosis, bone formation disorders, glaucoma and gastroparesis.

The combinations according to the invention can be used alone or, if required, in combination with other active ingredients. The present invention further provides medicaments comprising at least one of the combinations according to the invention and one or more further active ingredients, especially for the treatment and/or prophylaxis of the aforementioned disorders. Preferred examples of suitable combination active ingredients include:

hypotensive active ingredients, by way of example and with preference from the group of angiotensin AII antagonists, ACE inhibitors, calcium antagonists, endothelin antagonists, renin inhibitors, alpha receptor blockers, beta receptor blockers, mineralocorticoid receptor antagonists and also the diuretics;

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2, 5 and/or 9, especially PDE 5 inhibitors such as sildenafil, vardenafil and tadalafil;

antithrombotics, by way of example and with preference from the group of the platelet aggregation inhibitors, the anticoagulants or the profibrinolytic substances;

active compounds which alter lipid metabolism, by way of example and with preference from the group of thyroid receptor agonists, cholesterol synthesis inhibitors, preferred examples being HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the combinations according to the invention are administered in combination with a platelet aggregation inhibitor, by way of example and with preference aspirin, clopidogrel, ticlopidine or dipyridamole.

In a preferred embodiment of the invention, the combinations according to the invention are administered in combination with a thrombin inhibitor, by way of example and with preference ximelagatran, dabigatran, melagatran, bivalirudin or clexane.

In a preferred embodiment, the combinations according to the invention are administered in combination with a GPIIb/IIIa antagonist, by way of example and with preference tirofiban or abciximab.

In a preferred embodiment of the invention, the combinations according to the invention are administered in combination with a factor Xa inhibitor, by way of example and with preference rivaroxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the combinations according to the invention are administered in combination with heparin or with a low molecular weight (LMW) heparin derivative.

In a preferred embodiment of the invention, the combinations according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha receptor blockers, beta receptor blockers, mineralocorticoid receptor antagonists, and the diuretics.

In a preferred embodiment of the invention, the combinations according to the invention are administered in combination with a calcium antagonist, by way of example and with preference nifedipine, amlodipine, verapamil or diltiazem.

In a preferred embodiment of the invention, the combinations according to the invention are administered in combination with an alpha-1 receptor blocker, by way of example and with preference prazosin.

In a preferred embodiment of the invention, the combinations according to the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the combinations according to the invention are administered in combination with an angiotensin AII antagonist, by way of example and with preference losartan, candesartan, valsartan, telmisartan or embursatan.

In a preferred embodiment of the invention, the combinations according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the combinations according to the invention are administered in combination with an endothelin antagonist, by way of example and with preference bosentan, darusentan, ambrisentan or sitaxsentan.

In a preferred embodiment of the invention, the combinations according to the invention are administered in combination with a renin inhibitor, by way of example and with preference aliskiren, SPP-600 or SPP-800.

In a preferred embodiment of the invention, the combinations according to the invention are administered in combination with a mineralocorticoid receptor antagonist, by way of example and with preference spironolactone or eplerenone.

In a preferred embodiment of the invention, the combinations according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the combinations according to the invention are administered in combination with a CETP inhibitor, by way of example and with preference dalcetrapib, BAY 60-5521, anacetrapib or CETP vaccine (CETi-1).

In a preferred embodiment of the invention, the combinations according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the combinations according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the combinations according to the invention are administered in combination with a squalene synthesis inhibitor, by way of example and with preference BMS-188494 or TAK-475.

In a preferred embodiment of the invention, the combinations according to the invention are administered in combination with an ACAT inhibitor, by way of example and with preference avasimibe, melinamide, pactimibe, eflucimibe or SMP-797.

In a preferred embodiment of the invention, the combinations according to the invention are administered in combination with an MTP inhibitor, by way of example and with preference implitapide, BMS-201038, R-103757 or JTT-130.

In a preferred embodiment of the invention, the combinations according to the invention are administered in combination with a PPAR-gamma agonist, by way of example and with preference pioglitazone or rosiglitazone.

In a preferred embodiment of the invention, the combinations according to the invention are administered in combination with a PPAR-delta agonist, by way of example and with preference GW 501516 or BAY 68-5042.

In a preferred embodiment of the invention, the combinations according to the invention are administered in combination with a cholesterol absorption inhibitor, by way of example and with preference ezetimibe, tiqueside or pamaqueside.

In a preferred embodiment of the invention, the combinations according to the invention are administered in combination with a lipase inhibitor, by way of example and with preference orlistat.

In a preferred embodiment of the invention, the combinations according to the invention are administered in combination with a polymeric bile acid adsorber, by way of example and with preference cholestyramine, colestipol, colesolvam, CholestaGel or colestimide.

In a preferred embodiment of the invention, the combinations according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the combinations according to the invention are administered in combination with a lipoprotein(a) antagonist, by way of example and with preference gemcabene calcium (CI-1027) or nicotinic acid.

In the combinations according to the invention, the components can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The combinations according to the invention can be administered in administration forms suitable for these administration routes.

Suitable administration forms for oral administration are those which function according to the prior art and release the combinations according to the invention rapidly and/or in a modified manner and which contain the compounds, which are constituents of the combination, in crystalline and/or amorphized and/or dissolved form, for example tablets (non-coated or coated tablets, for example with gastric juice-resistant or retarded-dissolution or insoluble coatings which control the release of the compounds on which the combinations according to the invention are based), tablets or films/wafers which disintegrate rapidly in the oral cavity, films/lyophilizates, capsules (for example hard or soft gelatin capsules), sugar-coated tablets, granules, pellets, powders, emulsions, suspensions, aerosols or solutions.

Preferred administration forms include tablet forms (non-coated or coated tablets, for example with gastric juice-resistant or retarded-dissolution or insoluble coatings, which control the release of the compounds on which the combinations according to the invention are based), tablets or films/wafers which disintegrate rapidly in the oral cavity and particularly preferred administration forms are tablet forms (non-coated or coated tablets, for example with gastric juice-resistant or retarded-dissolution or insoluble coatings, which control the release of the components on which the combinations according to the invention are based), tablets or films/wafers which disintegrate rapidly in the oral cavity.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include inter alia preparations for injection and infusion in the form of solutions, suspensions, emulsions, lyophilizates or sterile powders.

For the other administration routes, suitable examples are inhalation medicaments (including powder inhalers, nebulizers), nasal drops, solutions or sprays, tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, dusting powders, implants or stents.

Preference is given to oral or parenteral administration, oral administration being more preferred. Particular preference is given to oral administration by means of tablet form.

In the combinations according to the invention, the components can be converted into the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavor and/or odour correctors.

In the combinations according to the invention, the components may be administered together or successively or separately in a combined unit dosage form, in two separate unit dosage forms, or in three separate unit dosage forms. The unit dosage form may also be a fixed combination.

A therapeutically effective amount of each component of the combination according to the invention may be administered simultaneously or sequentially in any sequence.

In one embodiment, the components may be present in a so-called delayed-release formulation in which the release of the components according to the invention takes place at different times. By way of example, mention may be made of a tablet with delayed-release dissolution coatings, each of which contains one or more components of the combinations according to the invention.

In one embodiment of the invention, in the case of oral administration, the dose of the sGC stimulator and/or sGC activator is around 1.25-20 mg, 1.25-5 mg od, around 5-10 mg od or 10 to 20 mg od.

In one embodiment of the invention, the dose of valsartan is around 20-110 mg bid, 20-50 mg bid or 50-110 mg bid.

In one embodiment of the invention, the dose of the NEP inhibitor is around 20-100 mg bid, around 20-50 mg bid or 50 to 100 mg bid.

In one embodiment of the invention, the dose of LCZ696 is around 40-400 mg, 50-200 mg bid, 50-100 mg bid or 100-200 mg bid.

In one embodiment of the invention, valsartan is provided in the form of a suitable unit dosage form, a capsule or tablet for example, and contains a therapeutically effective amount of, for example, 20 to 320 mg of valsartan, which can be administered to patients. The active ingredient may be administered three times a day, starting from a daily dose of 20 mg or 40 mg of valsartan for example, which increases over 80 mg daily and further to 160 mg daily to 320 mg daily. Preferably, valsartan is administered once a day or twice a day to patients with heart failure at a dose of 80 mg or 160 mg respectively. Corresponding doses can be taken, for example, in the morning, at noon or at night. In the case of heart failure, preference is given to q.d. or b.i.d. administration.

In one embodiment of the invention, the NEP inhibitor is administered in unit forms, tablets or capsules for example, which contain for example 20 mg to 800 mg, preferably 50 mg to 700 mg, more preferably 100 mg to 600 mg and even more preferably 100 mg to 300 mg, which are administered once a day.

The doses described above may be formulated in the context of the invention as a fixed dose combination in which the preferred unit forms may be tablets or capsules.

In a preferred embodiment of the invention, the dose of the sGC stimulator and/or sGC activator is about 2.5-20 mg od, the dose of valsartan is about 25 mg bid and the dose of the NEP inhibitor is about 25 mg bid, also preferably the dose of the sGC stimulator and/or sGC activator is about 2.5-20 mg od, the dose of valsartan is about 50 mg bid and the dose of the NEP inhibitor is about 50 mg bid and also preferably the dose of the sGC stimulator and/or sGC activator is about 2.5-20 mg od, the dose of valsartan is about 100 mg bid and the dose of the NEP inhibitor is about 100 mg bid.

In a preferred embodiment of the invention, the dose of the sGC stimulator and/or sGC activator is about 5-10 mg od, the dose of valsartan is about 25 mg bid and the dose of the NEP inhibitor is about 25 mg bid, also preferably the dose of the sGC stimulator and/or sGC activator is about 5-10 mg od, the dose of valsartan is about 50 mg bid and the dose of the NEP inhibitor is about 50 mg bid and also preferably the dose of the sGC stimulator and/or sGC activator is about 5-10 mg od, the dose of valsartan is about 100 mg bid and the dose of the NEP inhibitor is about 100 mg bid.

In a preferred embodiment of the invention, the dose of the sGC stimulator and/or sGC activator is about 2.5-5 mg od, the dose of valsartan is about 25 mg bid and the dose of the NEP inhibitor is about 25 mg bid, also preferably the dose of the sGC stimulator and/or sGC activator is about 2.5-5 mg od, the dose of valsartan is about 50 mg bid and the dose of the NEP inhibitor is about 50 mg bid and also preferably the dose of the sGC stimulator and/or sGC activator is about 2.5-5 mg od, the dose of valsartan is about 100 mg bid and the dose of the NEP inhibitor is about 100 mg bid.

In a preferred embodiment of the invention, the dose of the sGC stimulator and/or sGC activator is about 10-20 mg od, the dose of valsartan is about 25 mg bid and the dose of the NEP inhibitor is about 25 mg bid, also preferably the dose of the sGC stimulator and/or sGC activator is about 10-20 mg od, the dose of valsartan is about 50 mg bid and the dose of the NEP inhibitor is about 50 mg bid and also preferably the dose of the sGC stimulator and/or sGC activator is about 10-20 mg od, the dose of valsartan is about 100 mg bid and the dose of the NEP inhibitor is about 100 mg bid.

In a further preferred embodiment of the invention, the dose of the sGC stimulator and/or sGC activator is about 2.5-20 mg od and the dose of LCZ696 is about 50 mg bid, also preferably the dose of the sGC stimulator and/or sGC activator is about 5-10 mg od and the of LCZ696 is about 100 mg bid and also preferably the dose of the sGC stimulator or sGC activator is about 2.5-5 mg od and the dose of LCZ696 is about 200 mg bid.

In a further preferred embodiment of the invention, the dose of the sGC stimulator and/or sGC activator is about 10-20 mg od and the dose of LCZ696 is about 50 mg bid, also preferably the dose of the sGC stimulator and/or sGC activator is about 10-20 mg od and the of LCZ696 is about 100 mg bid and also preferably the dose of the sGC stimulator and/or sGC activator is about 10-20 mg od and the dose of LCZ696 is about 200 mg bid.

In a further preferred embodiment of the invention, the dose of the sGC stimulator and/or sGC activator is about 2.5-5 mg od and the dose of LCZ696 is about 50 mg bid, also preferably the dose of the sGC stimulator and/or sGC activator is about 2.5-5 mg od and the of LCZ696 is about 100 mg bid and also preferably the dose of the sGC stimulator and/or sGC activator is about 2.5-5 mg od and the dose of LCZ696 is about 200 mg bid.

In a further preferred embodiment of the invention, the dose of the sGC stimulator and/or sGC activator is about 5-10 mg od and the dose of LCZ696 is about 50 mg bid, also preferably the dose of the sGC stimulator and/or sGC activator is about 5-10 mg od and the of LCZ696 is about 100 mg bid and also preferably the dose of the sGC stimulator and/or sGC activator is about 5-10 mg od and the dose of LCZ696 is about 200 mg bid.

It may nevertheless be necessary in some cases to deviate from the stated amounts, and specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

Experimental Section

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for liquid/liquid solutions are based in each case on volume.

Assessment of Physiological Efficacy

The suitability of the combinations according to the invention for treating cardiovascular disorders can be demonstrated in the following assay systems:

Radiotelemetric Measurement of Blood Pressure and Heart Rate of Conscious Rats

A commercially available telemetry system from Data Sciences International DSI, USA, was employed for the measurements on conscious rats (Wistar strain Unilever/WU or Spontaneous Hypertensive Rat/SHR) described below. The system consists of 3 main components: (1) implantable transmitters (PhysioTel® telemetry transmitter), (2) receivers (PhysioTel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies are conducted on adult female rats with a body weight of >200 g. After transmitter implantation, the experimental animals are housed singly in type III Makrolon® cages. They have free access to standard feed and water. The day/night rhythm in the test laboratory is set by changing the illumination of the room.

Transmitter Implantation:

The telemetry transmitters used (e.g. PA-C40 HD-S10, DSI) are surgically implanted under aseptic conditions in the experimental animals at least 14 days before the first experimental use.

For the implantation, the fasted animals are anesthetized with isoflurane (IsoFlo®, Abbott, initiation 5%, maintenance 2%) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vetbond™, 3M). The transmitter housing is fixed intraperitoneally to the abdominal wall muscle, and the wound is closed layer by layer. Post-operatively, an antibiotic (Ursocyclin® 10%, 60 mg/kg s.c., 0.06 ml/100 g body weight, Serumwerk Bernburg AG, Germany) for infection prophylaxis and an analgesic (Rimadyl®, 4 mg/kg s.c., Pfizer, Germany) are administered.

Substances and Solutions:

Unless stated otherwise, the substances to be studied are administered orally to a group of animals in each case (n=6). In accordance with an administration volume of 2 ml/kg of body weight, the test substances are dissolved in suitable solvent mixtures. A solvent-treated group of animals is used as control.

Experimental Outline:

The telemetry measuring system is configured for 24 animals.

Each of the instrumented rats living in the system is assigned a separate receiving antenna (RPC-1 Receiver, DSI). The implanted senders can be activated externally via an installed magnetic switch and are switched to transmission during the pre-run of the experiment. The signals emitted can be detected online by a data acquisition system (Dataquest™ A.R.T. for Windows, DSI or Ponemah, DSI) and processed accordingly.

In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT). These parameters are measured over 24 hours after administration.

The acquisition of measurements is repeated under computer control at 5-minute intervals. The source data obtained as absolute values are corrected in the diagram with the currently measured barometric pressure (Ambient Pressure Reference Monitor, APR-1, DSI).

Evaluation:

After the end of the experiment, the acquired individual data are sorted using the analysis software (Dataquest™ A.R.T. 4.1 Analysis or Ponemah, DSI). The 2 hour time point before substance administration is assumed as the blank value.

The data are smoothed over a presettable period by determination of the means (30 minute mean).

Literature:

K. Witte, K. Hu, J. Swiatek, C. MUssig, G. Ertl and B. Lemmer, Experimental heart failure in rats: effects on cardiovascular circadian rhythms and on myocardial β-adrenergic signaling, Cardiovasc. Res. 47 (2): 203-405, 2000.

Long-Term Study in Ren-2 Transgenic Rats Treated with L-NAME

The cardiovascular effect after administration of an sGC modulator, neprilysin inhibitor, angiotensin AII antagonist and double and triple combinations thereof are demonstrated by determining the long-term effects on hemodynamic and hormonal parameters in a high renin, low-NO blood pressure model in rats.

Male transgenic Ren-2 rats (TGR(mRen2)27) are raised on-site and kept under controlled light and temperature conditions. From an age of 10 to 20 weeks the animals are randomized into different groups. The control group receive a placebo, the test groups sGC modulators, neprilysin inhibitors, angiotensin AII antagonists and double and triple combinations thereof for 4-10 weeks. The rats of the placebo and treatment groups also receive 30-100 mg/l L-NAME via drinking water. The test substances are administered p.o. as a suspension in a mixture of transcutol/cremophor/water (10/20/70=v/v/v) or as a tylose suspension. Systolic blood pressure and heart rate are measured weekly using the "tail-cuff" method in conscious animals in cages at a constant temperature of 37° C. Urine collections occur on day 0, during and at the end of the experiment in metabolism cages and proteinuria, urinary electrolyte excretion are determined. At the end of the studies, left ventricular pressure and cardiac contraction are measured under anesthesia. Finally, the animals are sacrificed by decapitation and blood samples withdrawn. Plasma and urine parameters are biochemically determined, e.g. ANP (RIA Kit RK 005-24, Phoenix Pharmaceuticals, Inc., USA), cGMP (RIA Kit RE29075, IBL International GmbH, Germany), renin, angiotensin I (RIA Kit CA-1533, DiaSorin S.p.A., Italy) and aldosterone (P2714, DiaSorin S.p.A., Italy). Organs, e.g. kidney, heart, lungs etc. are taken and gene expression profiles and histopathological data are collected.

Hypertensive Heart Failure Model in Dogs

The cardiovascular effect after administration of an sGC modulator (sGC stimulator or sGC activator), neprilysin inhibitor, angiotensin AII antagonist, and double and triple combinations thereof are evaluated in a dog model of "mild" systolic heart failure caused by angiotensin AII antagonist-induced acute hypertension. An experimental animal model of left ventricular dysfunction is triggered by right ventricular "tachypacing" at 180 bpm for 10 days. The experimental implementation of this model has been described in detail. [Redfield et al., Circulation 1993; 87:2016-2022]

Hypertensive "Renal Wrap" Dogs

The effect of an sGC modulator (sGC stimulator or sGC activator), neprilysin inhibitor, angiotensin AII antagonist, and double and triple combinations thereof on blood pressure and heart rate are tested in the hypertensive "renal wrap" dog model. In the model a kidney is wrapped with silk, while the second kidney is subjected to an occlusion of the main kidney artery. [Page et al., Science 1939; 89: 2307-2308; Goldblatt et al., Proc Natl Acad Sci 1976; 73: 1722-1724]. About 4 weeks after the operation, the dogs develop stable high blood pressure.

Results:

Results are shown in FIGS. 1 and 2 for the compound of the formula (6) in a triple combination with a neprilysin inhibitor and an angiotensin AII antagonist compared to the single administration of the compound of the formula (6) and a double combination of a neprilysin inhibitor and an angiotensin AII antagonist.

The compound of the formula (6) shows no hemodynamic effects (blood pressure, heart rate) at an oral dose of 0.1 mg/kg; at 0.3 mg/kg a decrease in the mean arterial blood pressure of ca. −10% and a transient increase in heart rate was observed. The comparative substances, which are administered orally as a double combination, show a decrease in the mean arterial blood pressure of ca. −20% with associated reflex tachycardia at the dose investigated. The addition of 0.1 mg/kg of the compound of the formula (6) to the double combination leads, compared with the double combination alone, to a reduced reflexive increase in the heart rate with the same decrease in the mean arterial blood pressure.

The combination of the compound of the formula (6) at a dose of 0.3 mg/kg with a neprilysin inhibitor and an angiotensin AII antagonist shows an additional effect on the blood pressure decrease. Surprisingly, a non-additive effect on the heart rate was observed in the triple-combination trial (no additive compensatory effect or reflex tachycardia). In the double and triple combination, 30 mg/kg sacubitril and 10 mg/kg valsartan is used.

Results are shown in FIGS. 3, 4 and 5 for the compound of the formula (29) in a triple combination with a neprilysin inhibitor and an angiotensin AII antagonist compared to the single administration of the compound of the formula (29) and a double combination of a neprilysin inhibitor and an angiotensin AII antagonist.

The compound of the formula (29) shows a decrease in the mean arterial blood pressure of ca. −10% or 15% and an associated reflex tachycardia at an oral dose of 3 mg/kg and 10 mg/kg. The compound of the formula (29) shows reflex tachycardia at an oral dose of 1 mg/kg. The comparative substances, which are administered orally as a double combination, show a decrease in the mean arterial blood pressure of ca. −15% at the dose investigated. The triple combination of the compound of the formula (29) with a neprilysin inhibitor and an angiotensin AII antagonist shows an effect on the blood pressure decrease. In the double and triple combination, 30 mg/kg sacubitril and 10 mg/kg valsartan is used.

Figure 1:
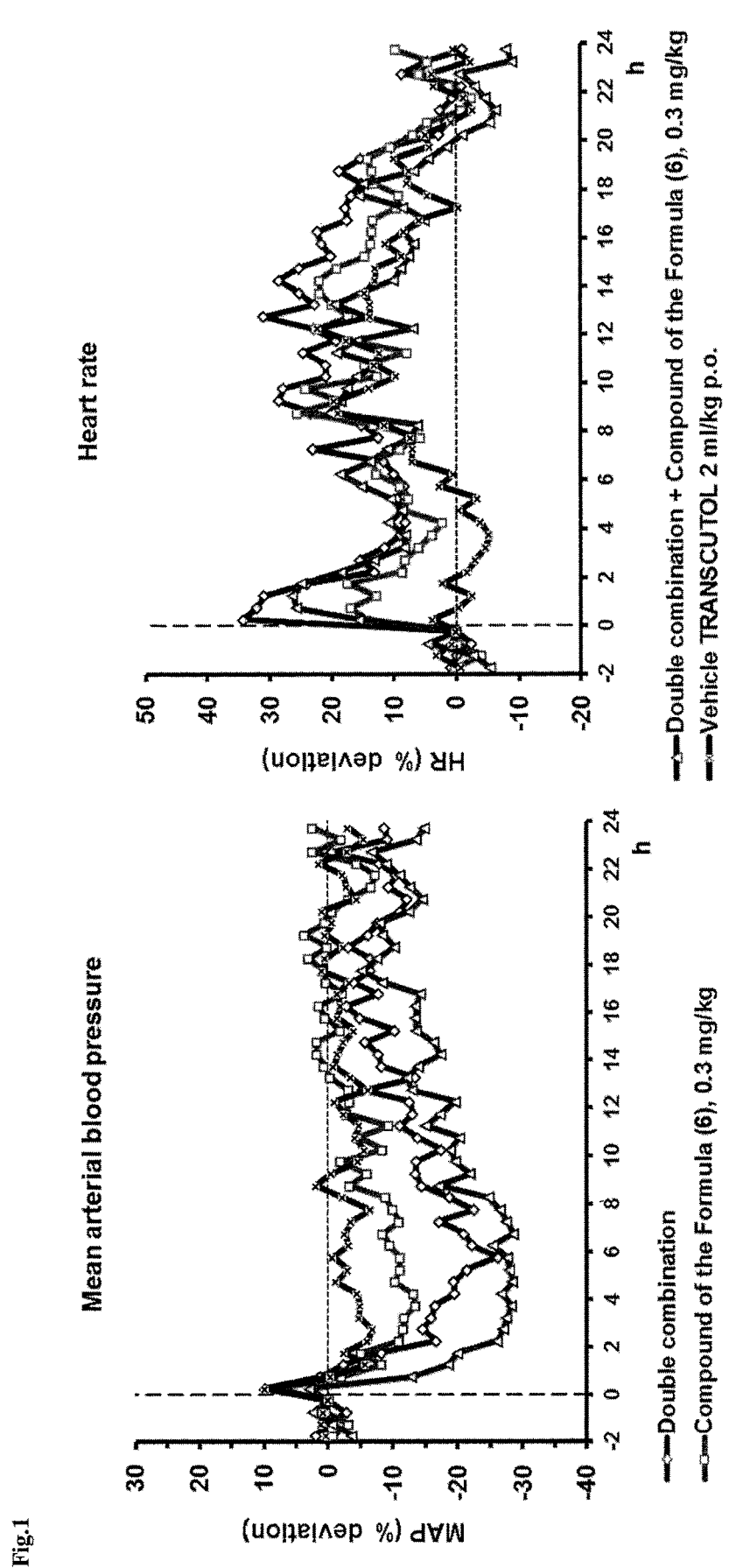
FIG. 1: B-x) mean arterial blood pressure and heart rate as % deviation versus time [h] after substance administration; compound of the formula (6), 0.3 mg/kg p.o.; double combination: 30 mg/kg sacubitril and 10 mg/kg valsartan p.o., triple combination: compound of the formula (6), 0.3 mg/kg, 30 mg/kg sacubitril and 10 mg/kg valsartan p.o.
Figure 2:
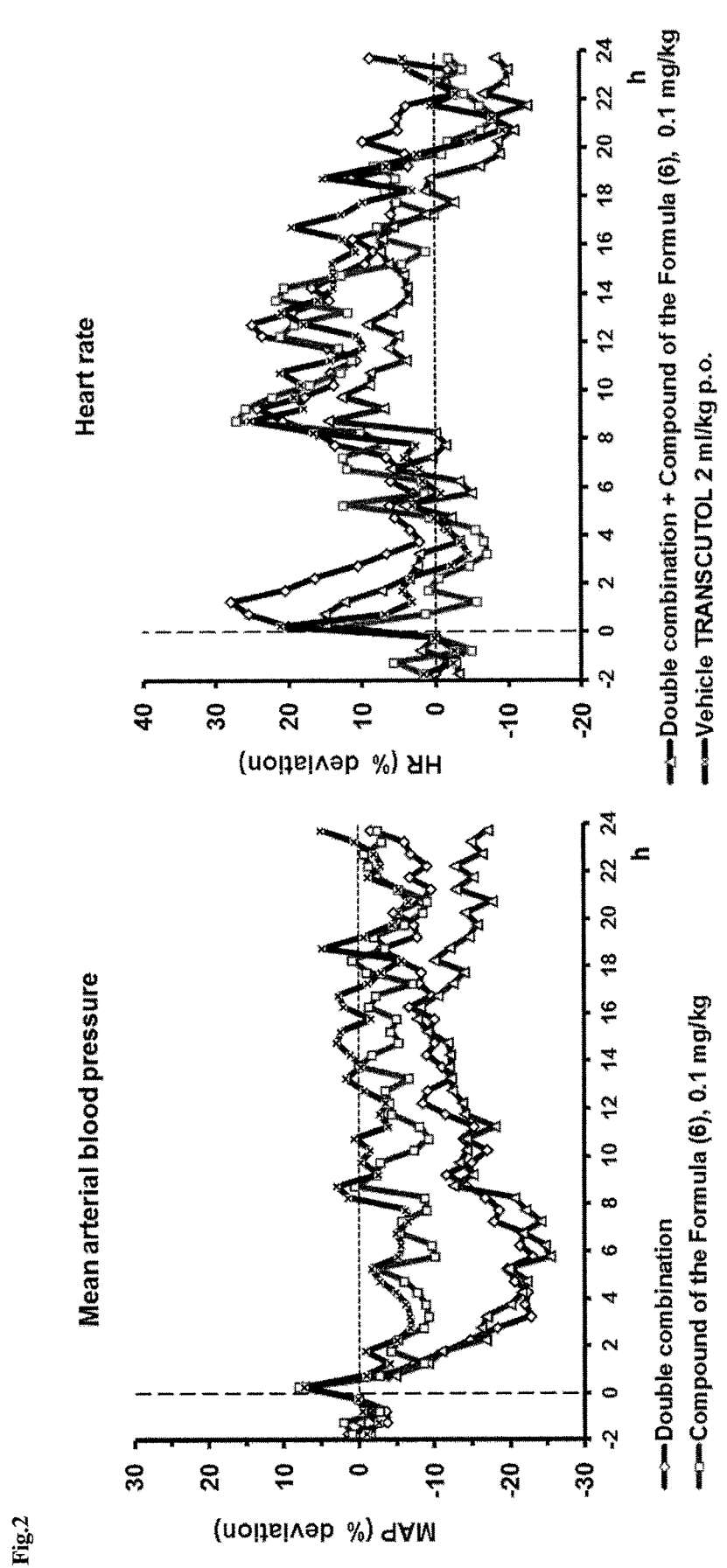
FIG. 2: B-x) mean arterial blood pressure and heart rate as % deviation versus time [h] after substance administration; compound of the formula (6), 0.1 mg/kg p.o.; double combination: 30 mg/kg sacubitril and 10 mg/kg valsartan p.o., triple combination: compound of the formula (6), 0.1 mg/kg, 30 mg/kg sacubitril and 10 mg/kg valsartan p.o.
Figure 3:
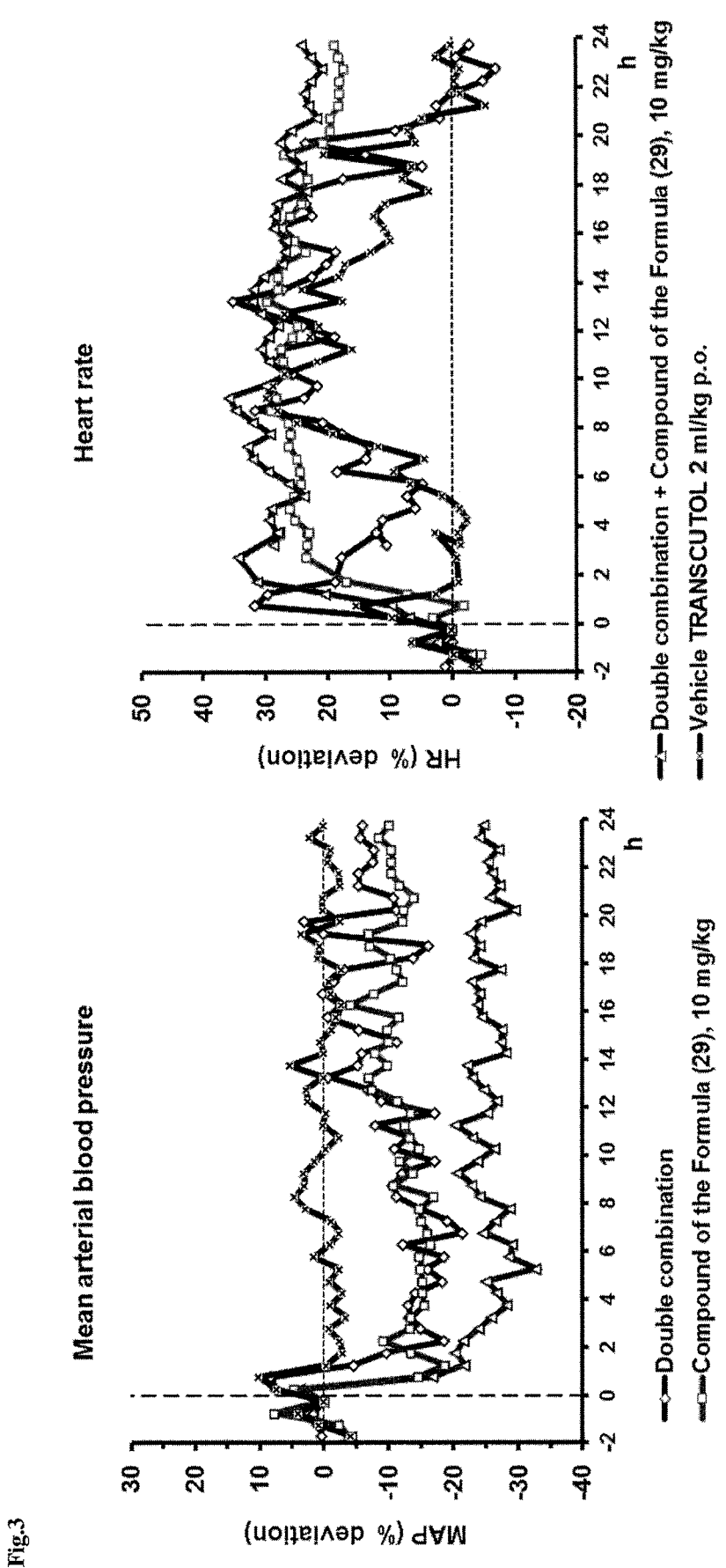
FIG. 3: B-x) mean arterial blood pressure and heart rate as % deviation versus time [h] after substance administration; compound of the formula (29), 10 mg/kg p.o.; double combination: 30 mg/kg sacubitril and 10 mg/kg valsartan p.o., triple combination: compound of the formula (29), 10 mg/kg, 30 mg/kg sacubitril and 10 mg/kg valsartan p.o.
Figure 4:
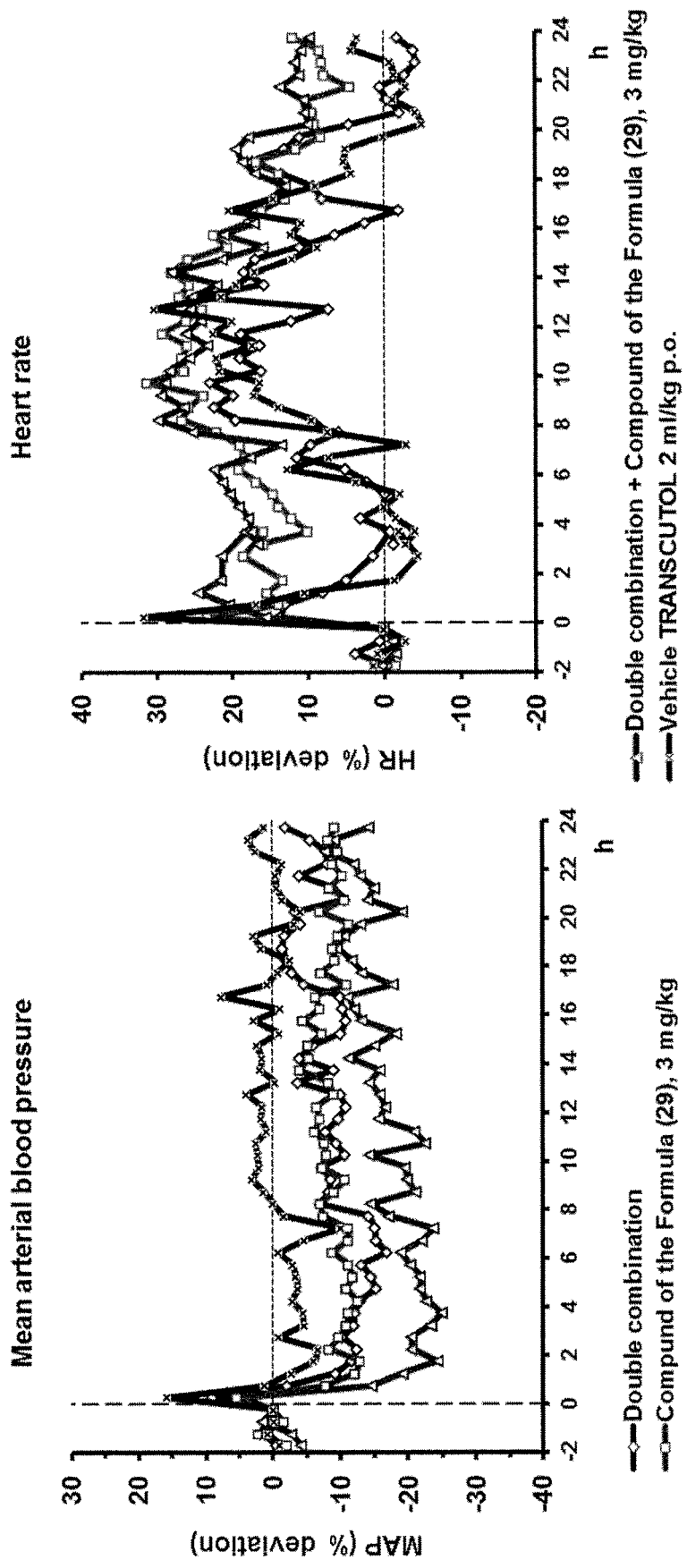
FIG. 4: B-x) mean arterial blood pressure and heart rate as % deviation versus time [h] after substance administration; compound of the formula (29), 3 mg/kg p.o.; double combination: 30 mg/kg sacubitril and 10 mg/kg valsartan p.o., triple combination: compound of the formula (29), 3 mg/kg, 30 mg/kg sacubitril and 10 mg/kg valsartan p.o.
Figure 5:
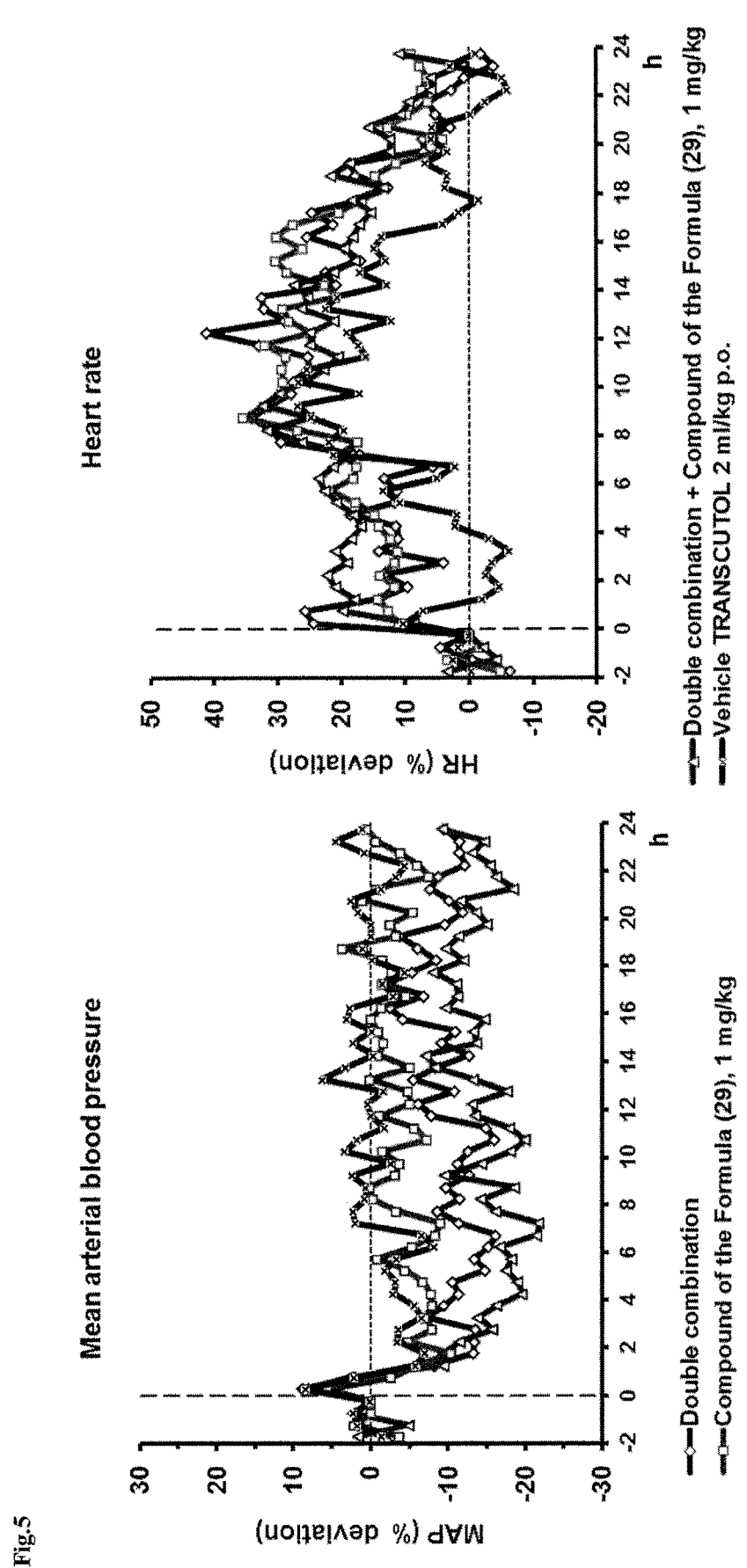
FIG. 5: B-x) mean arterial blood pressure and heart rate as % deviation versus time [h] after substance administration; compound of the formula (29), 1 mg/kg p.o.; double combination: 30 mg/kg sacubitril and 10 mg/kg valsartan p.o., triple combination: compound of the formula (29), 1 mg/kg, 30 mg/kg sacubitril and 10 mg/kg valsartan p.o.

The invention claimed is:

1. A method for the treatment of cardiovascular disorders, renal disorders, lung disorders, and fibrotic disorders in humans and animals comprising administering to a patient in need thereof a therapeutically effective amount of (1) an sGC modulator selected from the group consisting of sGC stimulators and sGC activators; (2) sacubitril; and (3) valsartan and also in each case the salts, solvates and solvates of the salts thereof.

2. The method of claim 1, wherein sacubitril and valsartan are administered as trisodium [3-((1S,3R)-1-biphenyl-4-yl-methyl-3-ethoxycarbonyl-1-butylcarbamoyl)propionate-(S)-3'-methyl-2'-(pentanoyl{2"-(tetrazol-5-ylate)biphenyl-4'-ylmethyl}amino)butyrate] hemipentahydrate.

3. The method of claim 1, wherein the sGC modulator is an sGC stimulator selected from the group consisting of compounds of the formulae

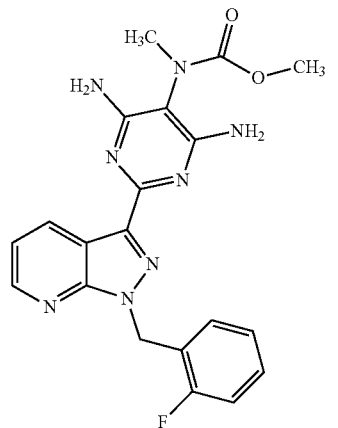
(3)

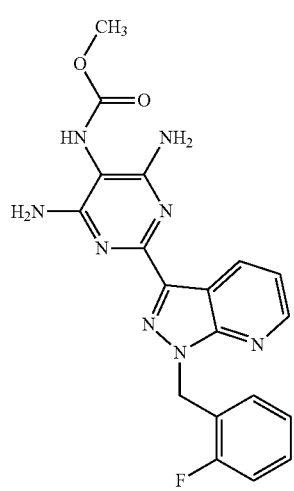
(4)

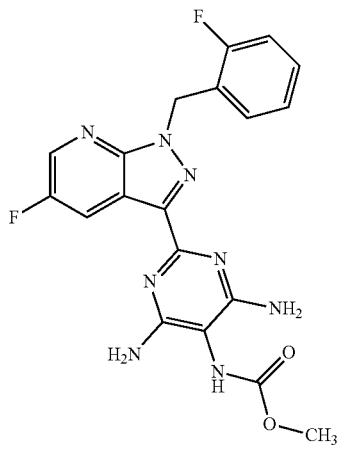
(6)

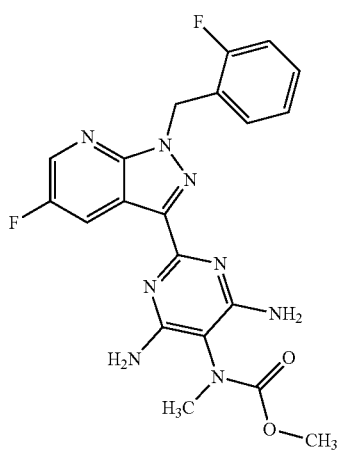
(7)

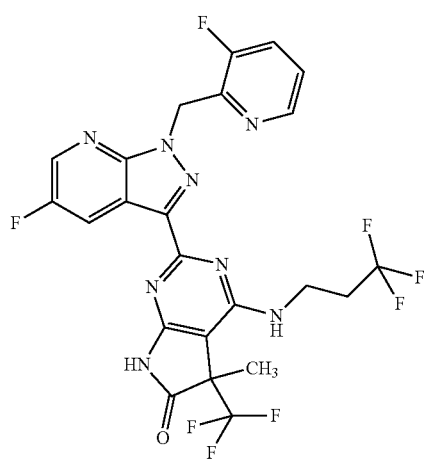
(28)

and salts, solvates and solvates of the salts of the compounds of formulae (3), (4), (6), (7) and (28), or is an sGC activator selected from the group consisting of a compound of the formula (29)

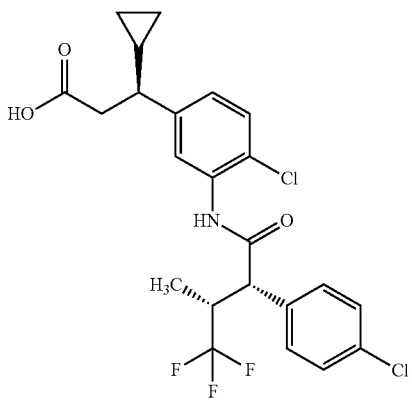

and salts, solvates, and solvates of the salts thereof.

4. The method of claim 3, wherein sacubitril and valsartan are present as tri sodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate.

5. The method of claim 1, wherein the sGC modulator is an sGC stimulator of the formula (6) or is an sGC activator of the formula (29) or a salt, solvate or solvate of a salt of the compound of formula (6) or of formula (29), and further wherein sacubitril and valsartan are present as trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate.

6. The method of claim 5, wherein the sGC modulator is an sGC activator of the formula (29) or a salt, solvate, or solvate of a salt thereof.

7. The method of claim 1, wherein the sGC modulator is an sGC stimulator of the formula (6) or is an sGC activator of the formula (29) or a salt, solvate or solvate of a salt of the compound of formula (6) or of formula (29).

8. The method of claim 1, wherein the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension; a renal disorder that is chronic kidney failure; or is diabetic retinopathy.

9. The method of claim 3, wherein the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension; a renal disorder that is chronic kidney failure; or is diabetic retinopathy.

10. The method of claim 5, wherein the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension; a renal disorder that is chronic kidney failure; or is diabetic retinopathy.

11. The method of claim 6, wherein the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension; a renal disorder that is chronic kidney failure; or is diabetic retinopathy.

12. The method of claim 7, wherein the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension; a renal disorder that is chronic kidney failure; or is diabetic retinopathy.

13. The method of claim 12, wherein
the sGC modulator is an sGC stimulator of the formula (6) or a salt, solvate or solvate of a salt thereof and the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension or
the sGC modulator is an sGC activator of the formula (29) or a salt, solvate or solvate of a salt thereof and the disorder being treated is a renal disorder that is chronic kidney failure, or is diabetic retinopathy.

14. The method of claim 13, wherein the sGC modulator is an sGC activator of the formula (29) or a salt, solvate or solvate of a salt of the compound of formula (29), and the disorder being treated is a renal disorder that is chronic kidney failure, or is diabetic retinopathy.

15. The method of claim 5, wherein
the sGC modulator is an sGC stimulator of the formula (6) and is administered at a dosage of 1.25-20 mg od and trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate is administered at a dosage of 100-200 mg or
the sGC modulator is an sGC activator of the formula (29) or a salt, solvate or solvate of a salt of the compound of formula (29) and trisodium [3-((1S,3R)-1-biphenyl-4-ylmethyl-3-ethoxycarbonyl-1-butylcarbamoyl)propionate-(S)-3'-methyl-2'-(pentanoyl{2''-(tetrazol-5-ylate)biphenyl-4'-ylmethyl}amino)butyrate] hemipentahydrate is administered at a dosage of 100-200 mg bid.

16. The method of claim 15, wherein the disorder being treated is a cardiovascular disorder selected from the group consisting of acute and chronic heart failure, heart failure with preserved ejection fraction, heart failure with reduced ejection fraction, diastolic heart failure, systolic heart failure, and acute phases of worsening of existing chronic heart failure, hypertension, and resistant hypertension; a renal disorder that is chronic kidney failure; or is diabetic retinopathy.

* * * * *